(12) United States Patent
Hart et al.

(10) Patent No.: US 7,083,626 B2
(45) Date of Patent: Aug. 1, 2006

(54) SURGICAL ACCESS DEVICE WITH PENDENT VALVE

(75) Inventors: Charles C. Hart, Summerville, SC (US); John R. Brustad, Dana Point, CA (US); Nabil Hilal, Laguna Niguel, CA (US); Henry Kahle, Trabuco Canyon, CA (US)

(73) Assignee: Applied Medical Resources Corporation, Rancho Santa Margarita, CA (US)

( * ) Notice: Subject to any disclaimer, the term of this patent is extended or adjusted under 35 U.S.C. 154(b) by 0 days.

(21) Appl. No.: 10/264,550

(22) Filed: Oct. 4, 2002

(65) Prior Publication Data

US 2004/0068232 A1 Apr. 8, 2004

(51) Int. Cl.
*A61F 11/00* (2006.01)

(52) U.S. Cl. ............... 606/108; 604/167.03; 604/264

(58) Field of Classification Search ........... 604/167.06, 604/164.02, 167.01–167.04, 264, 506, 30, 604/28, 23–26, 104; 606/108, 167, 170, 606/172, 185
See application file for complete search history.

(56) References Cited

U.S. PATENT DOCUMENTS

| | | | |
|---|---|---|---|
| 5,053,016 A | 10/1991 | Lander | |
| 5,116,353 A | 5/1992 | Green | |
| 5,197,955 A * | 3/1993 | Stephens et al. | 604/167.01 |
| 5,209,737 A | 5/1993 | Ritchart et al. | |
| 5,242,412 A | 9/1993 | Blake, III | |
| 5,290,245 A | 3/1994 | Dennis | |
| 5,300,036 A | 4/1994 | Mueller et al. | |
| 5,308,336 A | 5/1994 | Hart et al. | |
| 5,342,315 A * | 8/1994 | Rowe et al. | 604/167.06 |
| 5,354,280 A | 10/1994 | Haber et al. | |
| 5,385,553 A * | 1/1995 | Hart et al. | 604/167.03 |
| 5,391,153 A | 2/1995 | Haber et al. | |
| 5,411,483 A | 5/1995 | Loomas et al. | |
| 5,492,304 A | 2/1996 | Smith et al. | |
| 5,496,280 A * | 3/1996 | Vandenbroek et al. | 604/167.03 |
| 5,545,142 A * | 8/1996 | Stephens et al. | 604/167.01 |
| 5,554,124 A | 9/1996 | Alvarado | |
| 5,584,850 A * | 12/1996 | Hart et al. | 606/185 |
| 5,603,702 A * | 2/1997 | Smith et al. | 604/256 |
| 5,628,732 A | 5/1997 | Antoon, Jr. et al. | |
| 5,643,301 A | 7/1997 | Mollenauer | |
| 5,657,963 A * | 8/1997 | Hinchliffe et al. | 251/149.1 |
| 5,720,759 A * | 2/1998 | Green et al. | 606/167 |
| 5,727,770 A | 3/1998 | Dennis | |

(Continued)

OTHER PUBLICATIONS

Laparoscopic Colorectal Surgery—Jeffrey W. Milsom, Bartholomäus Böhm; (1966) Springer-Verlag New York, Inc. p. 25.

(Continued)

*Primary Examiner*—Cris Rodriguez
(74) *Attorney, Agent, or Firm*—Richard L. Myers; Patrick Y. Ikehara

(57) ABSTRACT

A surgical access device, such as a trocar, includes a pendent valve having an elongate structure extending from a proximal end to a septum valve disposed at a distal end. In operation, the elongate structure follows the angle of the instrument to pre-position the septum valve into the path of the instrument where it is not significantly challenged during instrument insertion or manipulation. The pendant valve can be made to float at both the proximal end and the distal end of the elongate structure, to further reduce the vulnerability of the septum valve. Since the valve is less vulnerable to instrument insertion, it can be formed to minimize friction and maximize the functional range of the access device.

18 Claims, 20 Drawing Sheets

U.S. PATENT DOCUMENTS

| | | | |
|---|---|---|---|
| 5,752,938 A | 5/1998 | Flatland et al. | |
| 5,792,113 A * | 8/1998 | Kramer et al. | 604/167.01 |
| 5,820,600 A | 10/1998 | Carlson et al. | |
| 5,865,812 A * | 2/1999 | Correia | 604/248 |
| 5,957,888 A * | 9/1999 | Hinchliffe | 604/117 |
| 6,066,117 A * | 5/2000 | Fox et al. | 604/249 |
| 6,123,689 A * | 9/2000 | To et al. | 604/256 |
| 6,162,196 A * | 12/2000 | Hart et al. | 604/167.02 |
| 6,217,555 B1 * | 4/2001 | Hart et al. | 604/167.01 |
| 6,228,061 B1 | 5/2001 | Flatland et al. | |
| 6,258,065 B1 | 7/2001 | Dennis et al. | |
| 6,551,282 B1 | 4/2003 | Exline et al. | |
| 6,595,946 B1 | 7/2003 | Pasqualucci | |
| 6,702,787 B1 | 3/2004 | Racenet et al. | |
| 6,726,663 B1 | 4/2004 | Dennis | |
| 2002/0013552 A1 | 1/2002 | Dennis et al. | |
| 2003/0004529 A1 | 1/2003 | Tsonton et al. | |
| 2004/0066008 A1 | 4/2004 | Smith | |

OTHER PUBLICATIONS

Patent Cooperation Treaty, International Search Report, International Application No. PCT/US03/29442 dated Jan. 23, 2004.

* cited by examiner

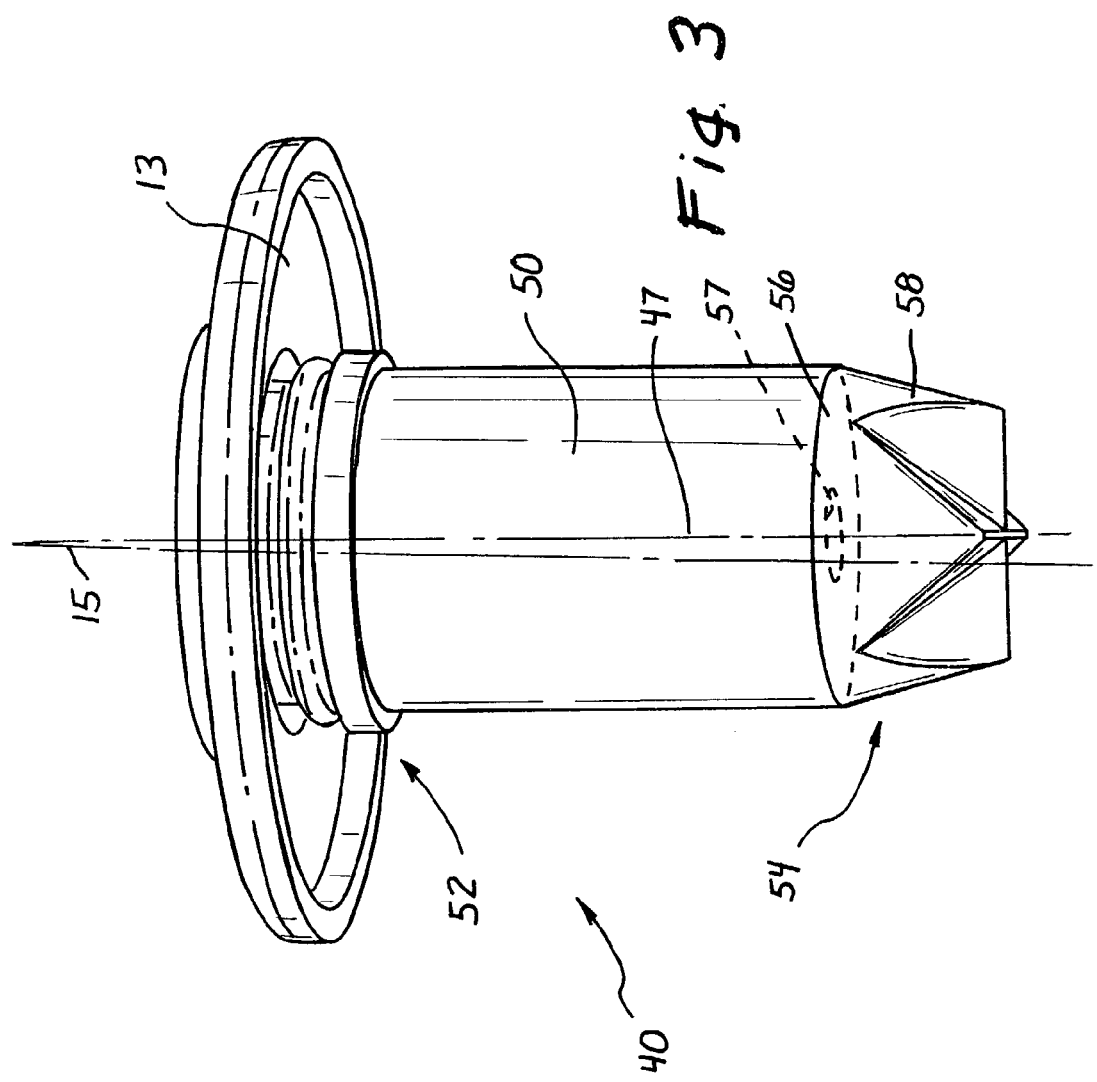

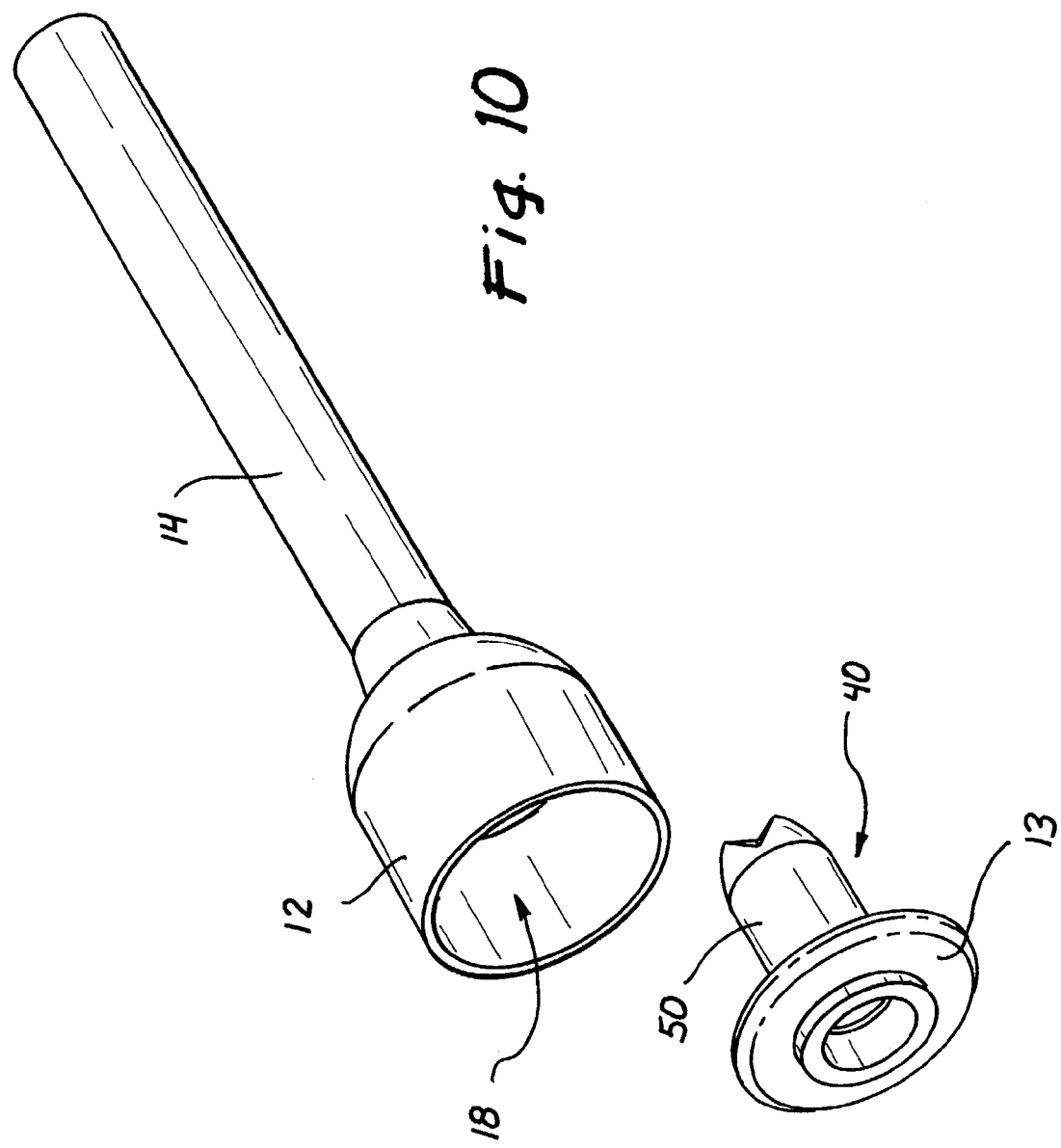

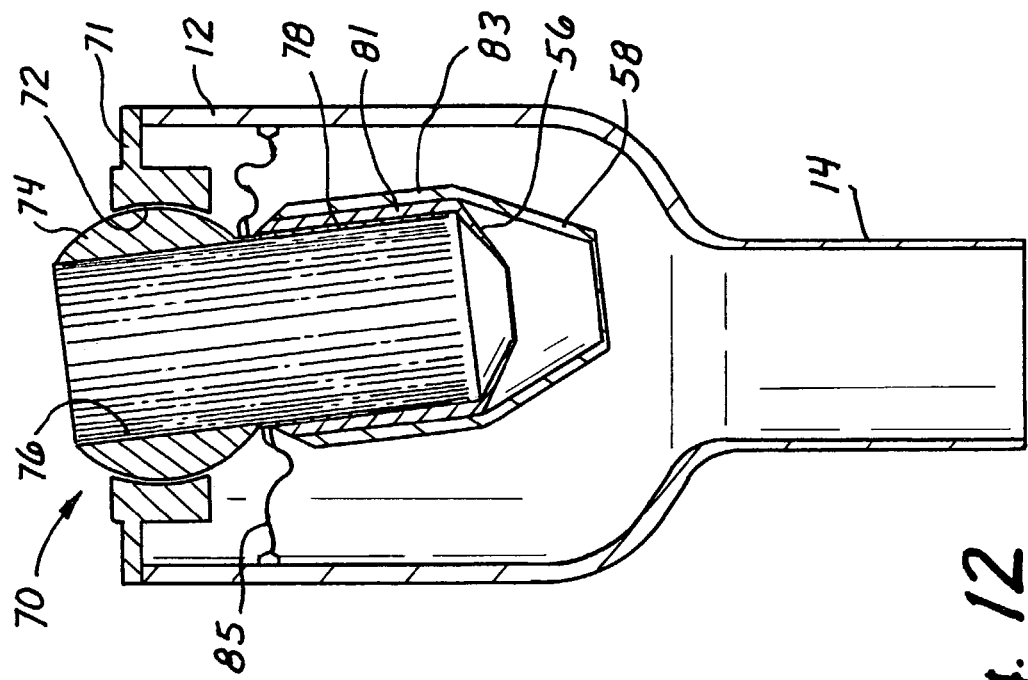
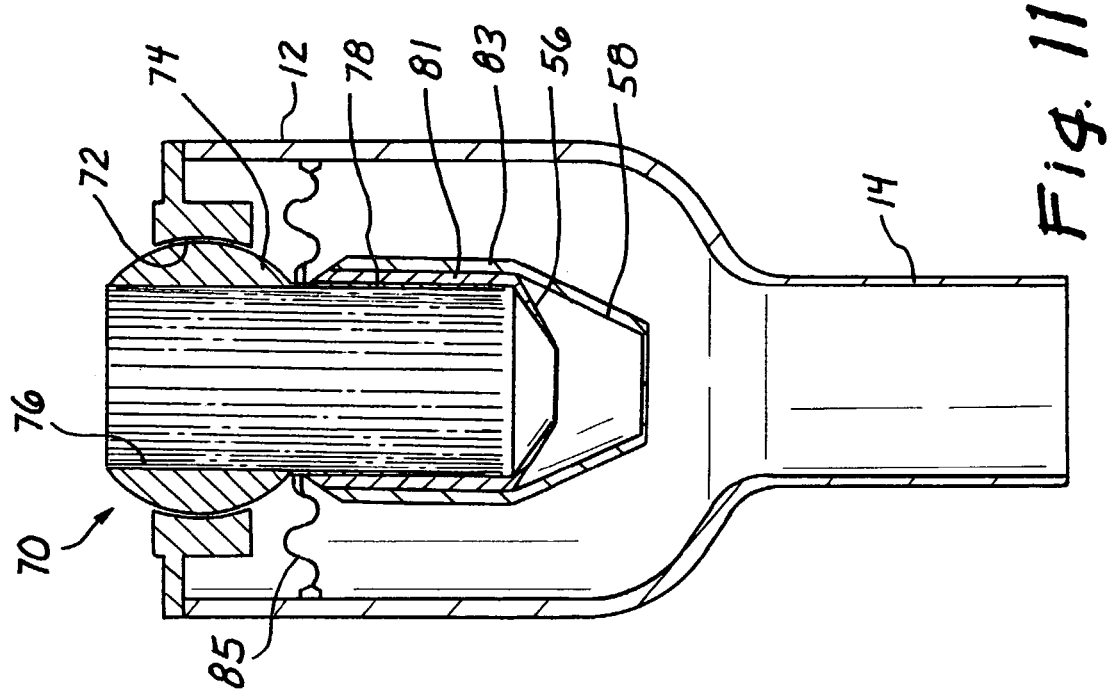
Fig. 11
Fig. 12

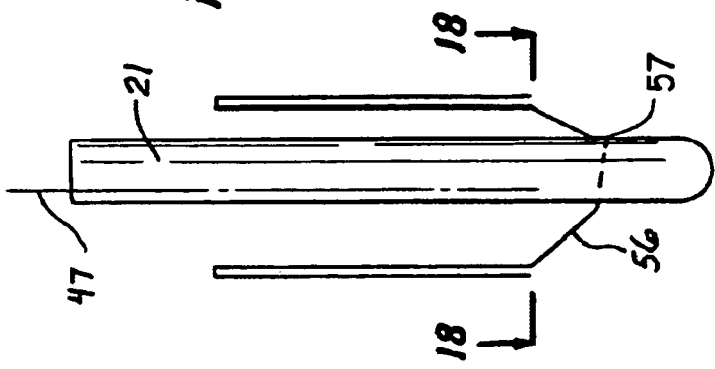
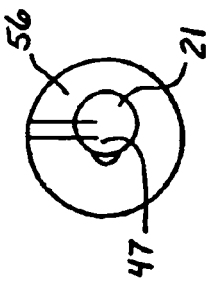
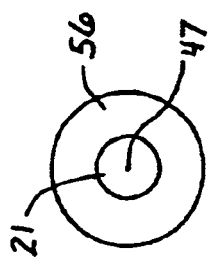
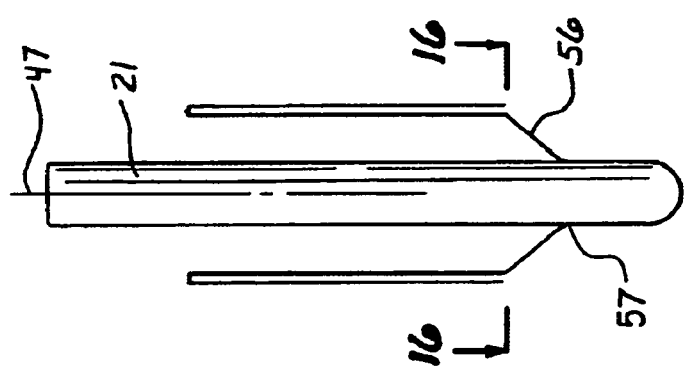

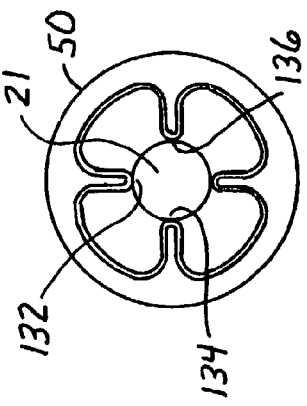
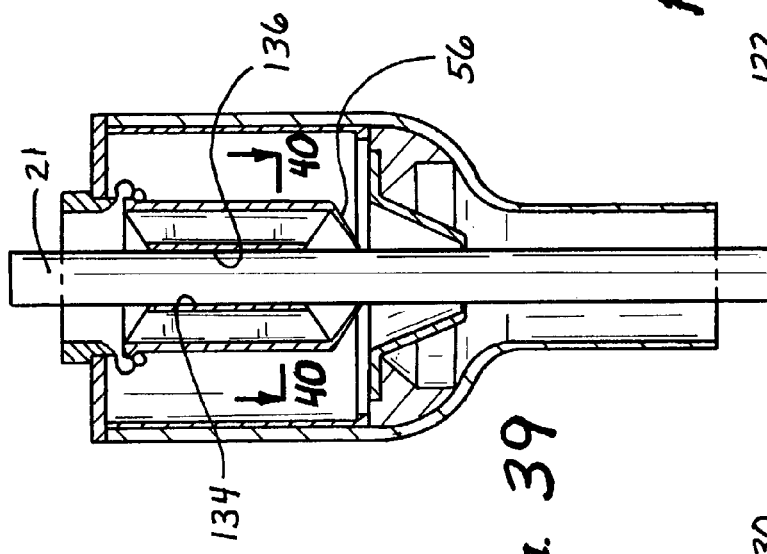
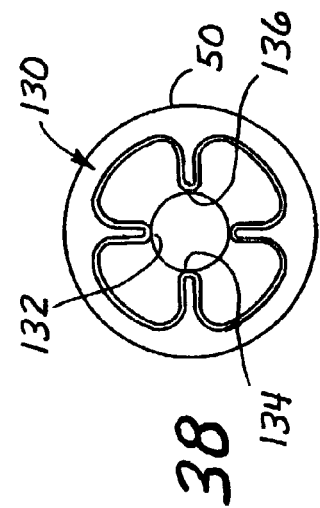
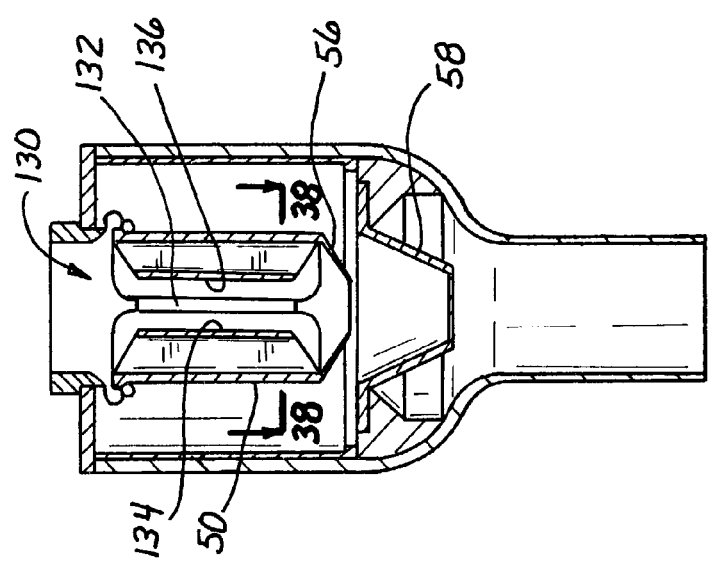

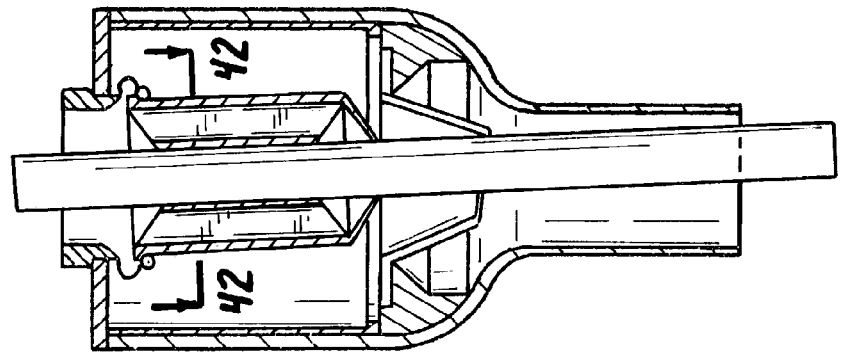
Fig. 41
Fig. 42
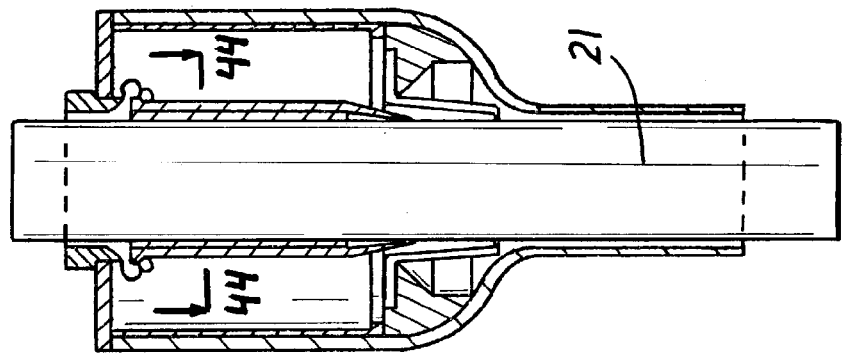
Fig. 43
Fig. 44

SURGICAL ACCESS DEVICE WITH PENDENT VALVE

BACKGROUND OF THE INVENTION

Laparoscopic surgery is commonly performed using trocars having septum valves and zero valves which provide instrument access across an abdominal wall and into a gas pressurized abdominal cavity. The functional requirements of such valves can be many and varied. In some embodiments the valves should be very durable even when challenged by the insertion of sharp-pointed instruments. They should be capable of accommodating a wide range of inserted instrumentation without leaking. They should be nearly friction-free so that they do not interfere with the action of the instrument. And, of course, they should not damage the inserted instruments. In addition, they should be cost-effective and user-friendly, and they should not add to the complexity of a surgical procedure.

There are presently many trocars and trocar valves that attempt to address the needs of laparoscopic surgeries. Perhaps most notable of these is the trocar structure which includes a "floating" septum seal as disclosed and claimed in U.S. Pat. No. 5,385,553. In this patent, a septum valve is disclosed with a movable attachment portion which permits the sealing orifice of the septum valve to follow the lateral movement of an inserted instrument. This movement or "float" of the septum valve is accommodated primarily in a two-dimensional plane which is disposed generally perpendicular to the axis of the trocar. As the instrument is moved laterally, the septum valve floats so that the sealing orifice remains generally round thereby maintaining a strong sealing relationship with the instrument. The floating septum allows the use of a delicate, larger bore septum since the floating orifice is not inordinately challenged or elongated as the inserted instrument is manipulated.

In comparison, a septum valve that does not float must be constructed of very durable material and provided with a very small orifice in order to maintain a gas-tight sealing relationship with the inserted instrument. The tradeoff in this case is friction and sensitivity. By floating the septum valve, laparoscopic trocars have been made more durable and sensitive.

In several existing "floating" systems, the "float" has been provided only in a lateral direction. As a result, the desirable floating characteristics are available only when the instrument is in place. This leaves even the floating valves vulnerable to instruments upon insertion. Instruments having sharp points can be particularly detrimental to the valve structure.

Elongate tubular structures of the past have not functioned in the manner of the present invention. For example, the tubular structure disclosed in U.S. Pat. No. 5,492,304 does not function to guide a seal into alignment with the instrument, but rather is provided merely to change the size of a septum valve. Similarly, the tubular structure in U.S. Pat. No. 5,820,600 does not pendulate and is not coupled to a septum valve which is disposed distally of a pivot point.

Laparoscopic surgery is an evolving modality. Significant changes in instrumentation have challenged even the best trocar valves presently in use. Accordingly, there remains a continuing need to extend the range, durability and sensitivity of trocar valves.

SUMMARY OF THE INVENTION

These deficiencies of the prior art are overcome with the present invention which provides a guided and suspended or pendulous trocar valve assembly. In various embodiments, this assembly aligns the valve with an instrument to be inserted, so that the valve orifice is positioned accurately to receive the instrument. In addition, the assembly partially aligns or guides the instrument toward this optimum position relative to the valve orifice. The suspended or pendulous valve assembly is connected to the housing through a flexible coupling which is responsive to the insertion angle and motion of the inserted instrument. As a result, the valve orifice is not significantly challenged during the insertion or manipulation of the instrument.

Since the valve orifice is not challenged in the manner of the past, it can be sized and configured to maximize the ease and safety with which the instrument can be inserted, adjusted or withdrawn through the valve assembly. With appropriate sizing, friction is reduced and the vulnerability of the valve assembly to sharp-pointed or misdirected instruments is minimized. The suspended valve assembly greatly improves the performance of the trocar. It increases the functional range of the trocar valves so that a wider range of instrument sizes can be accommodated. The valve assembly can also be manufactured with increased durability without sacrificing performance.

These and other features and advantages of the invention will be better understood with reference to preferred embodiments and the associated drawings.

DESCRIPTION OF THE DRAWINGS

FIG. 3 is a perspective view of a pendent valve of the present invention mounted to an end cap of a trocar;

FIG. 10 is a perspective view illustrating removal of a trocar end cap and associated pendent valve to clear the working channel of the trocar;

FIG. 11 is an axial cross-section view of another embodiment of the pendent valve;

FIG. 12 is an axial cross-section view of the pendent valve illustrated in FIG. 11, showing the valve in a pivoted, floating disposition;

FIG. 15 is a schematic view of a fixed septum valve showing an instrument inserted along the axis of the valve;

FIG. 16 is a cross-section view taken along lines 16—16 of FIG. 15;

FIG. 17 is a schematic view of a fixed septum valve showing an instrument moved off-axis and producing a cat-eye effect;

FIG. 18 is a cross-section view taken along lines 18—18 of FIG. 17;

FIG. 23 is a schematic view showing relatively low side-load effects associated with a relatively long valve module;

FIG. 24 is a cross-section view taken along lines 24—24 of FIG. 23;

FIG. 25 is a schematic view showing relatively high side-load effects with a relatively short valve module;

FIG. 26 is a cross-section view taken along lines 26—26 of FIG. 25;

FIG. 37 is an axial cross-section view of a proximal guidance structure;

FIG. 38 is a cross-section view taken along lines 38—38 of FIG. 37;

FIG. 39 is a an axial cross-section view of the embodiment of FIG. 37 with an instrument inserted axially through the guidance structure;

FIG. 40 is a cross-section view taken along lines 40—40 of FIG. 39;

FIG. 41 is an axial cross-section view illustrating an instrument moved off-axis in the embodiment of FIG. 37;

FIG. 42 is a cross-section view taken along lines 42—42 of FIG. 41;

FIG. 43 is an axial cross-section view of the embodiment of FIG. 37 with a large diameter instrument inserted through the guidance structure;

FIG. 44 is a cross-section view taken along lines 44—44 of FIG. 43;

DESCRIPTION OF PREFERRED EMBODIMENTS AND BEST MODE OF THE INVENTION

Figure 1A:
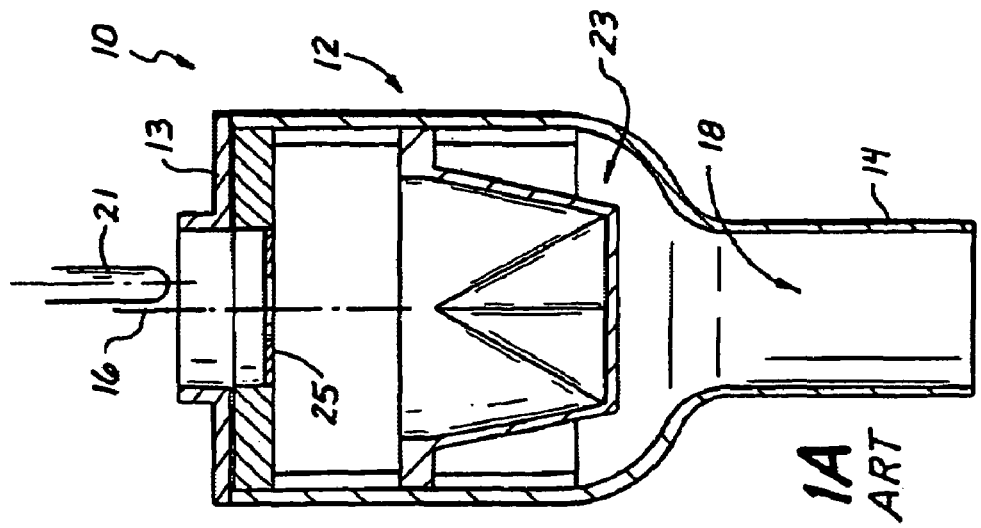
FIG. 1A is an axial cross-section view of a trocar of the prior art having a fixed septum valve for forming a seal with an inserted instrument.

A trocar is illustrated in FIG. 1A and designated by the reference numeral 10. This trocar 10 includes a housing 12, with an end cap 13, and a cannula 14. These three elements extend along a trocar axis 16 and define a working channel 18 for receipt of a surgical instrument 21. In the absence of the instrument 21, a zero valve 23 is provided to seal the working channel 18 and thereby preventing loss of insufflation gas. When the instrument 21 is present, a septum valve 25 forms an instrument seal with the instrument 21 in order to seal the working channel 18. When the instrument 21 is absent, the zero valve 23 closes on itself to seal the working channel 18.

Figure 1B:
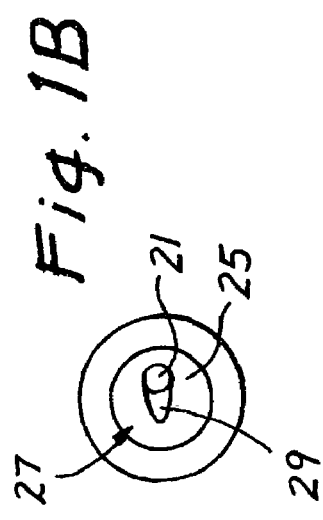
FIG. 1B is a top plan view of the fixed valve showing a cat-eye effect.

The trocar 10 illustrated in FIG. 1A is representative of the prior art in that the septum valve 25 is held in a generally fixed relationship with the housing 12. Unfortunately with this type of structure, when the instrument 21 is inserted or moved off axis, the septum valve 25 is stretched laterally and tends to form a cat-eye 27 as illustrated in the top view of FIG. 1B. The cat-eye 27 forms an undesirable opening 29 around the instrument 21 resulting in a loss of the insufflation gas.

Figure 2A:
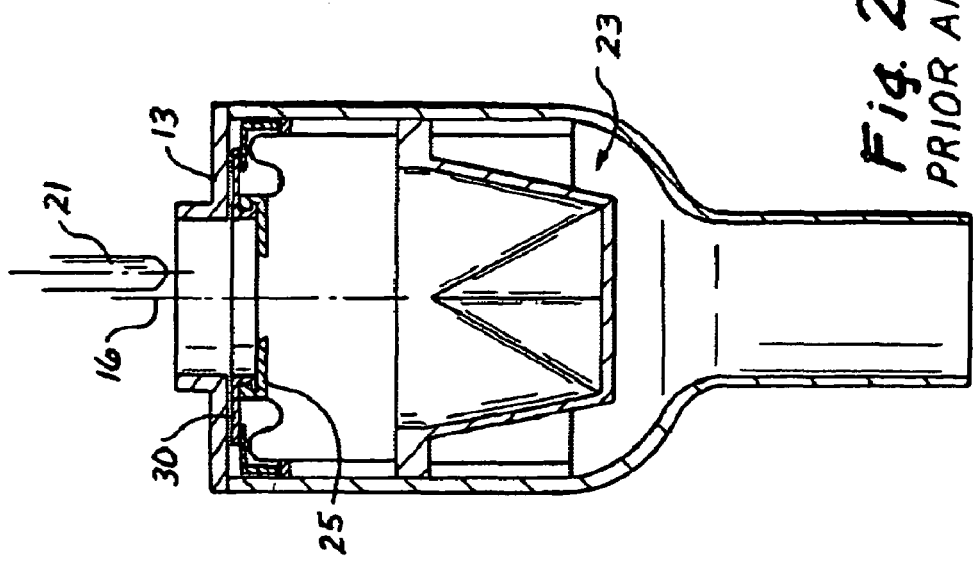
FIG. 2A is an axial cross-section view of a trocar having a septum valve which floats in two dimensions in accordance with the prior art.

Another trocar of the prior art is illustrated in FIG. 2A. In this case, the septum 25 is mounted on a floating structure 30 which is free to move laterally of the trocar axis 16. As the floating structure 30 moves laterally, it carries the septum valve 25 in an unstretched state. This enables the orifice of the septum valve 25 to move off-axis without changing its circular configuration. Thus, when the instrument 21 is inserted off-axis or moved off-axis, the septum valve 25 tends to avoid formation of the undesirable cat-eye 27.

Figure 2B:
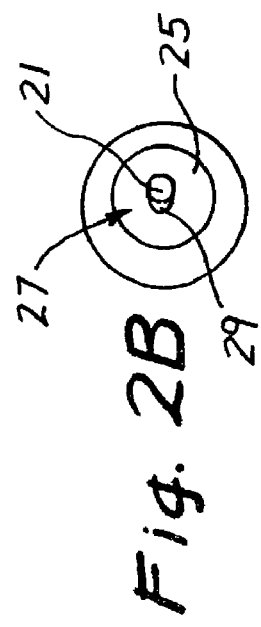
FIG. 2B is a top-plan view of the septum valve of FIG. 2A showing a slight cat-eye effect.
Figure 2C:
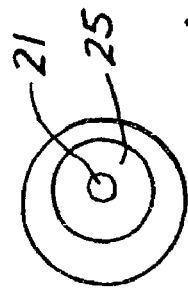
FIG. 2C is a top-plan view similar to FIG. 2B wherein the septum valve is strengthened to avoid even the slight cat-eye effect.

Nevertheless, there is some frictional resistance to movement of the floating structure 30. Until this resistance is overcome, there may be some lateral stretching of the septum valve 25, and some development of the cat-eye 27 as illustrated in FIG. 2B. In order to overcome even this slight cat-eye effect, the orifice of the septum valve 25 can be strengthened by making it smaller than the diameter of the instrument 21. Of course this reduced diameter increases the friction between the septum valve 25 and the instrument 21, and also reduces the overall range of instrument sizes which can be accommodated. Nevertheless, an off-axis round orifice can be achieved as illustrated in FIG. 2C.

Notwithstanding the advancements which lateral floating provides for the embodiment of FIG. 2A, as opposed to that of the embodiment of FIG. 1A, it remains an objective to advance certain desirable features for laparoscopic surgery in general, and for trocars in particular. For example, it is always desirable 1) to reduce instrument insertion forces, 2) to accommodate a larger range of instrument sizes with a single trocar structure, and 3) to accommodate forces commonly associated with the normal off-axis insertion and movement of the instrument 21.

Figure 4:
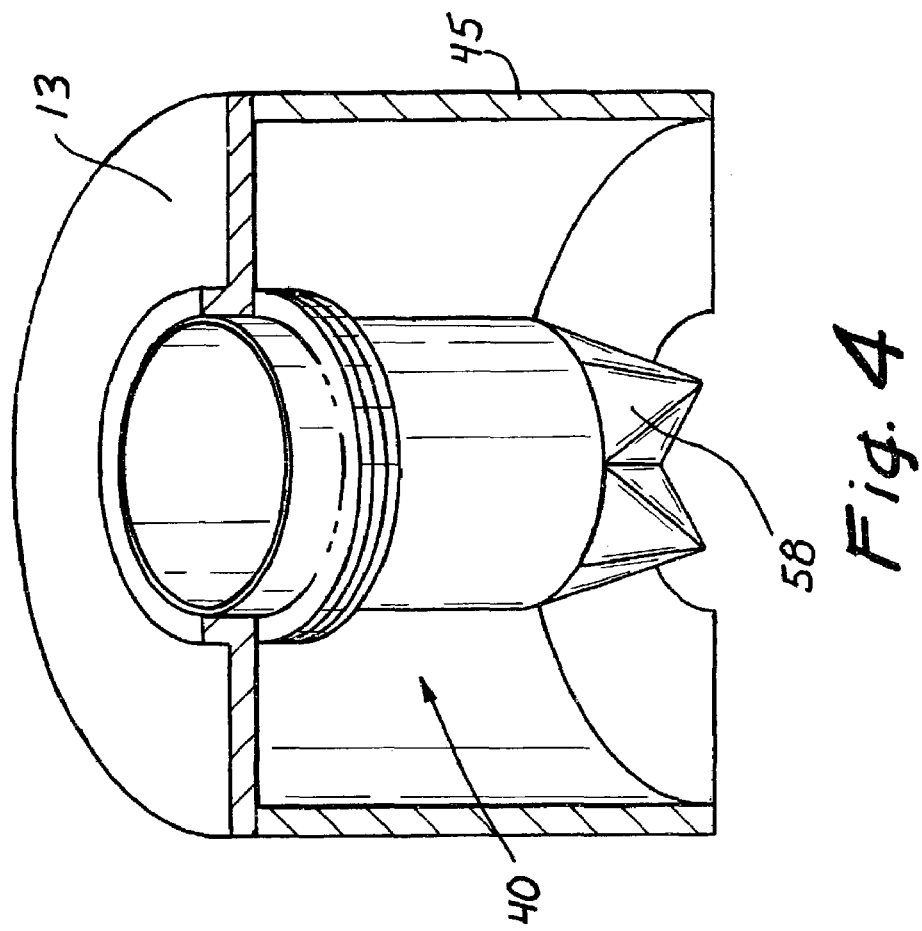
FIG. 4 is a perspective view of the pendent valve mounted to an end cap within a seal housing of a trocar.
Figure 6:
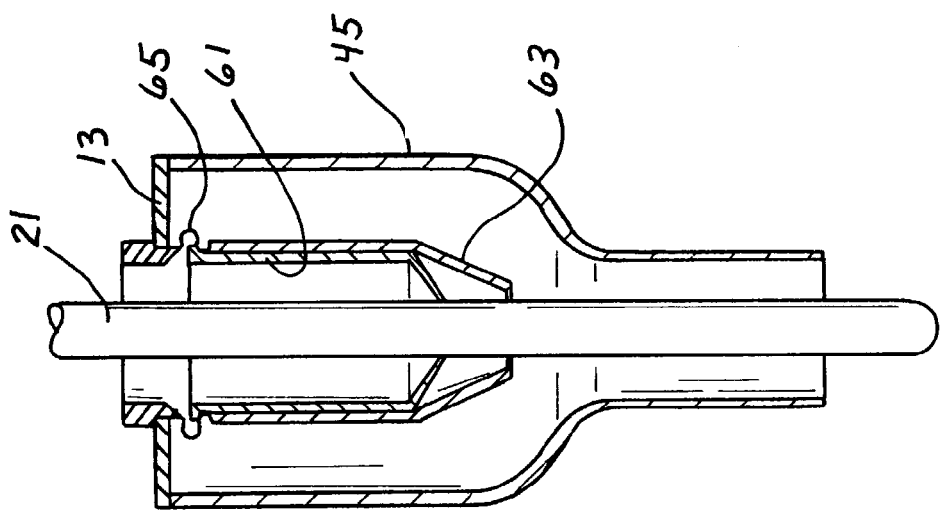
FIG. 6 is an axial cross-section view showing the pendent valve in operation with a relatively small diameter instrument.
Figure 5:
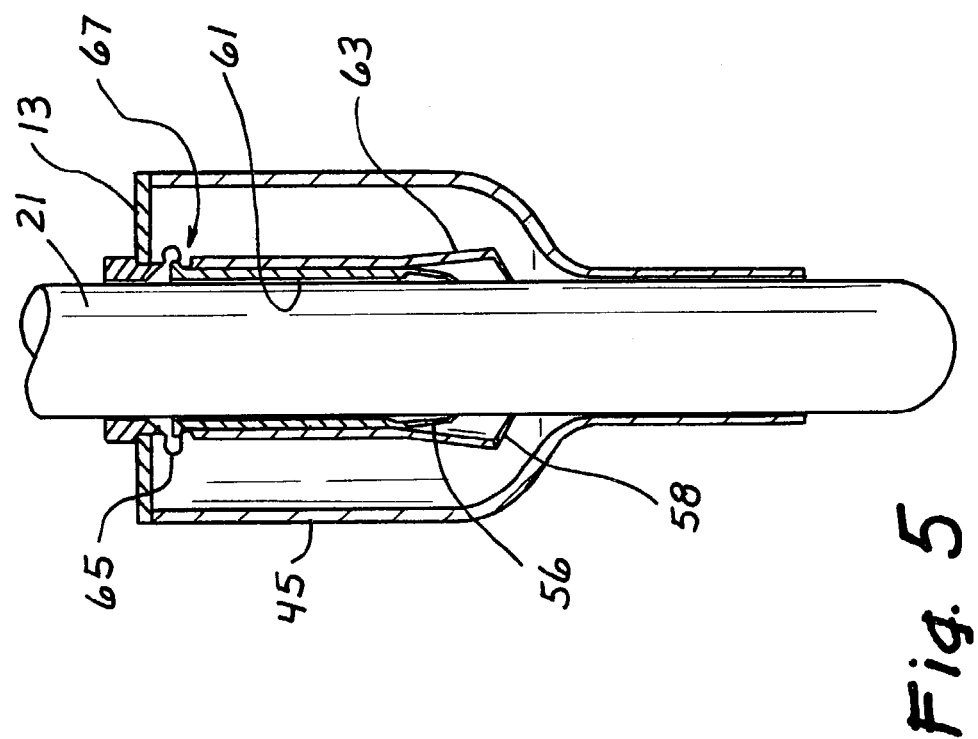
FIG. 5 is an axial cross-section view illustrating the pendent valve in operation with a relatively large diameter instrument.
Figure 8:
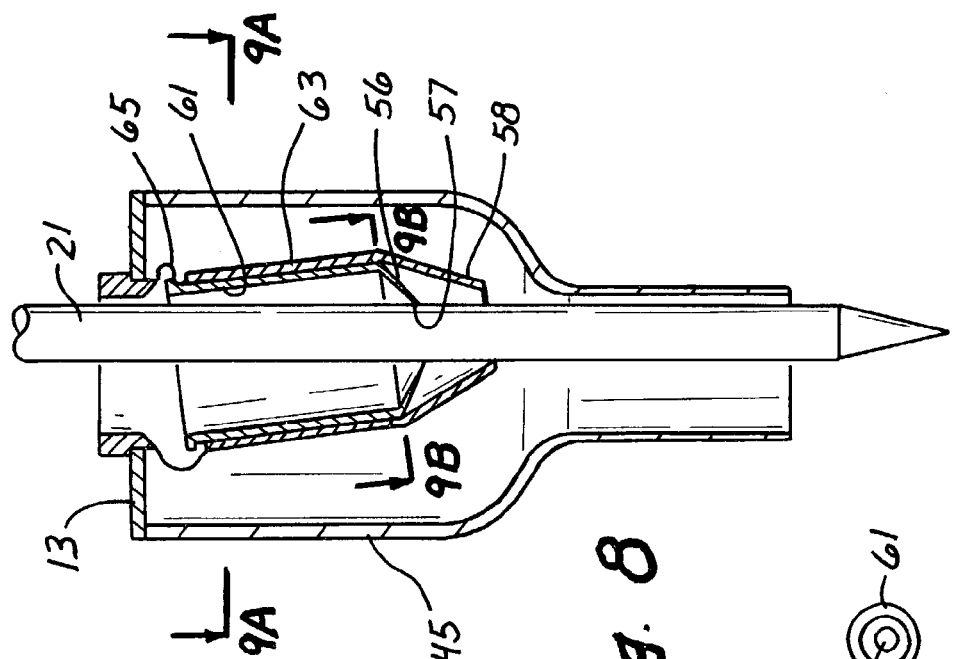
FIG. 8 is an axial cross-section view showing an instrument fully inserted with effective seal formation notwithstanding an off-axis position of the instrument.
Figure 9B:
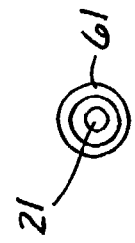
FIG. 9B is a cross-section view taken along lines 9—B of FIG. 8.

With reference to FIGS. 3–6, a preferred embodiment of the present invention comprises a suspended, pendent valve module 40 which can be mounted to an end cap 13 (FIG. 3), within a trocar housing 45 (FIG. 4), and adapted to receive a wide range of instrument sizes (FIGS. 5 and 6). As illustrated in FIGS. 3 and 4, the end cap 13 is typically disposed in a radial plain generally perpendicular to the axis 15 of the trocar 10. The module 40 also has an axis 47 and is characterized by an elongate tube 50 having a proximal end 52 and a distal end 54. In a preferred embodiment, the proximal end 52 is coupled to the end cap 13, while the distal end 54 carries a septum valve 56 with an orifice 57, and a zero valve 58.

The elongate tube 50 is of particular interest to the present invention as it provides the suspended or pendulous characteristics for the entire module 40, and most importantly for the valves 56 and 58 at the distal end 54. Although the elongate tube 50 is illustrated to have a generally cylindrical configuration, it can also be provided with a conical configuration with its largest diameter at the proximal end 52 and its smallest diameter at the distal end 54. This conical structure will add the further advantage of guiding the instrument 21 increasingly toward the preferred orientation with the valves 56 and 58. The elongate tube 50 is characterized by a ratio of its length to its maximum diameter. This ratio is advantageously in a range between 1 and 3, and typically about 2. However, ratios outside this range may offer certain advantages to a particular embodiment.

The elongate tube 50 can be formed of an elastomeric material such as polyurethane or, natural or synthetic rubber; or a rigid material such as metal or plastic. Importantly, in this embodiment attachment of the elongate tube 50 to any other structure of the trocar 10 occurs only at the proximal end 52 in order to maximize the suspended, pendulous characteristics of the module 40.

The proximal end 52 of the module 40 is coupled to the end cap 13 by a flexible bellows or other structure which facilitates a floating or free movement of the module axis 47 relative to the trocar axis 16. At the distal end 54, the elongate module 40, including the tube 50, is generally unattached to the end cap 13 or any other portion of the housing 45 as illustrated in FIG. 4. Thus, the module 40 with the elongate tube 50 attached at only one end, functions as a pendulum supported or suspended at the proximal end 52 but otherwise free to swing or pendulate, particularly at its distal end 54.

In comparison to the prior art embodiment of FIG. 2 which floats only in a two-dimensional plane perpendicular to the axis 16, the distal end 54 of the module 40 actually floats in three dimensions. In fact, a loci of points traversed by the pendulous module 40 tends to define, not a planar surface, but rather a spherical surface. With this pendulous structure, the module 40 is free to swing and offers substantially zero resistance to lateral movement. This characteristic is further enhanced by the length of the tube 50 which functions as a lever arm. As the instrument 21 is inserted, any lateral force caused by off-axis insertion or movement, is transferred through the lever arm to the attachment structure at the end cap 13, easily facilitating lateral alignment of the valves 56 and 58.

With substantially reduced resistance to lateral movement, the orifice 57 of the septum valve 56 need not be strengthened to overcome any cat-eye effect, such as that illustrated in FIG. 2B. Rather, the septum valve 56 can be provided with an orifice diameter only slightly smaller than the smallest instrument in the range of instrument sizes. With a diameter larger than that contemplated for the prior art embodiment of FIG. 2C, a wider range of instrument sizes can be accommodated. Notably, at the upper end of the range, even larger instrument sizes can be accommodated without exceeding an acceptable level of friction.

The larger diameter of the septum orifice 57 will also be appreciated with a reduced friction between the septum valve 56 and the instrument 21. By comparison with the tighter septums of the prior art, the user will experience instrument insertion and maneuverability which is substantially frictionless.

Referring now to FIGS. 5–10, it will be noted that the trocar 10 in this embodiment includes the pendent valve module 40 with a gas-tight seal that divides the working channel 18 of the trocar into two distinct regions. The first region of the working channel 18 comprises the cannula 14 open at its distal end, and a distal portion of the housing 12 that is closed at its proximal end by the valves 56, 58. The second region includes the lumen within the elongate tube 50 of the module 40 that is closed at its distal end by the valves 56, 58, and a proximal portion of the housing 12 that is open at its proximal end through the end cap 13. In the illustrated embodiment, gas-tight isolation is permitted between these two regions while facilitating instrument access through the working channel 18.

When there is no instrument within the working channel 18, the zero valve 58, such as a duckbill valve, is employed to interrupt communication. This duckbill valve forms a gas-tight seal when retrograde pressure is present. A double duckbill valve of the preferred embodiment forms a gas-tight seal at very low pressure, and advantageously is very easily interrupted by an inserted instrument. If a large instrument is inserted into the working channel of the trocar, it is guided through the lumen of the pendent valve module 40 to a most appropriate position for insertion through a distal septum and subsequently into the cannula of the trocar. If such a large instrument has sharp, irregular, forked or otherwise potentially damaging distal features, it is presented to the distal septum in a minimally threatening position.

If a small instrument is used in the trocar, the pendulous seal module accommodates the side-to-side motion of the instrument through the flexible or swiveling proximal connection to the cap or housing. If a small instrument having sharp, irregular, forked or otherwise threatening distal features is presented for insertion, the pendulous seal module can flex, swivel, or pendulate into a location where the septum orifice 57 is best positioned to receive the approaching instrument. The flexibility of the proximal seal module connection combined with the frusto-conical nature of the septum valve provides a very durable, friction-reducing combination.

In the illustrated embodiment, the module 40 is comprised of a first elongate tubular member 61 and a second, coaxial elongate tubular member 63. The first, innermost tubular member 61is formed or fitted with a frusto-conical valve at the distal end 54 and a connecting region at the proximal end 52. The second, outer tubular member 63 is formed or fitted with a duckbill valve at the distal end 54 and a highly flexible coupler 65 at the proximal end 52. In a preferred embodiment, the first inner tubular member 61 is coupled to a connection feature 67 within the wall of the second outer tubular member 63. The second, outer member 63 is connected through its flexible coupler 65 to the end cap 13. The two, coaxial tubular members 61, 63 form the seal module 40 that is supported by the highly flexible coupler 65 to the end cap 13 of the trocar 10. The lumen of the first, inner tubular member 61 is sized and configured to pass a large laparoscopic instrument with minimal clearance.

Figure 7:
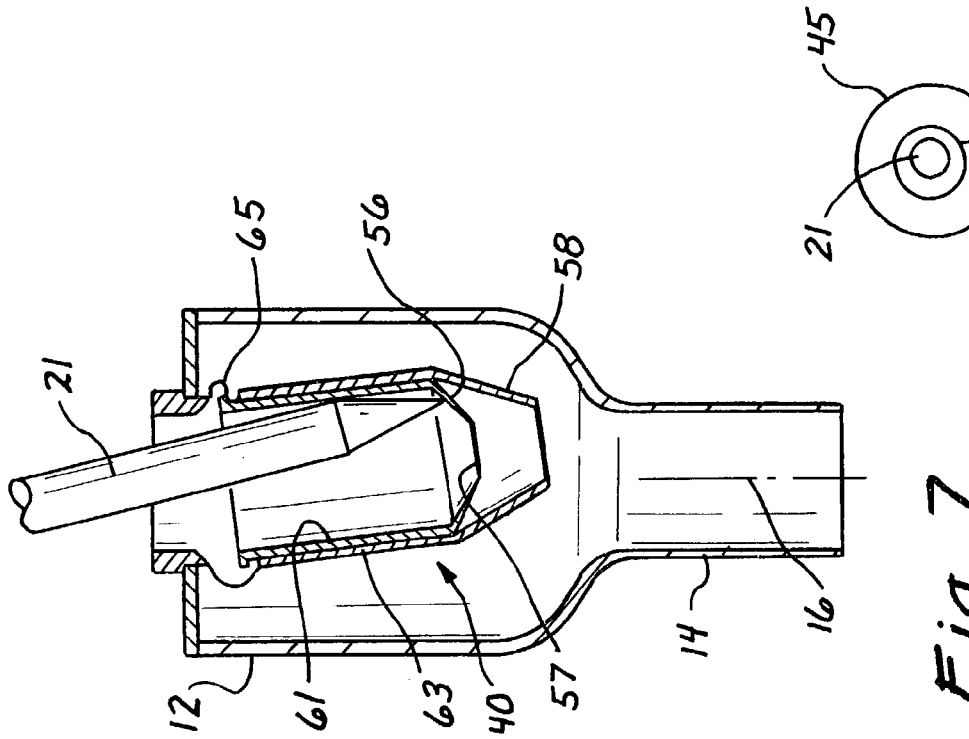
FIG. 7 is an axial cross-section view illustrating operation of the pendent valve during off-axis insertion of an instrument.
Figure 9A:
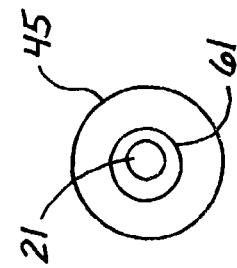
FIG. 9A is a cross-section view taken along lines 9—A of FIG. 8.

As best illustrated in FIG. 7, the instrument 21 will often be introduced at some angle to the axis 16 which will cause it to contact the inner surface of the tubular member 61. This will cause the pendent valve module 40 to pivot at the flexible coupler 65, thereby moving the septum valve 56 and its orifice 57 toward the distal tip of the instrument 21. If this tip contacts the frusto-conical edges of the valve 56, it would do so at a face angle which causes the orifice 57 to move further toward the instrument 21. This face angle is advantageously increased due to the pendulating characteristics of the module 40.

In this case, the highly flexible coupler 65 of the second tubular member comprises a series of thin, convoluted, folded or corrugated features that allow the pendulous seal module 40 to move from side-to-side, to bend, to rotate or otherwise to be positioned by the inserted or approaching instrument 21. An additional embodiment of the highly flexible coupler 65 may comprise a thin material that stretches and folds to achieve the same goals. An additional embodiment of the highly flexible coupler 65 may include a support region made of a low durometer material that achieves the same goals.

FIG. 10 illustrates another feature of the present invention wherein the pendulous module 40 is mounted on the distal face of the end cap 13. This structure enables the end cap 13 to be removed with the seal module 40 from the trocar housing 12 and integral cannula 14. With this feature, the entire working channel 18 can be cleared of any seal structure, thereby permitting the removal of large masses of tissue or other material from the surgical site. If all of the seal components are included in the module 40, removal of the end cap 13 leaves the trocar 10 with an unobstructed working channel 18.

A further embodiment of the highly flexible coupler 65 is illustrated in FIGS. 11 and 12. In this case, the coupler 65 includes a swiveling ball joint 70 to which the seal module 40 is connected. The ball joint 70 allows an inserted instrument to adjust the position of the septum valve 56 in order to prevent side loading and elongation of the septum orifice. The swivel connection in this embodiment comprises the end cap 13 with a socket 72 sized and configured to receive a ball 74 having a through hole 76 which communicates with the lumen of the trocar 10. The ball joint 70 has an elongate sleeve 78 that extends distally from the ball 74. This sleeve 78 is configured with an outer surface adapted to receive a first elongate seal member 81, which carries the septum valve 56, and a second elongate seal member 83 which carries the zero valve 58.

In this case, the three coaxial elements, the extended ball sleeve 78, the first seal member 81, and the second seal member 83, together with the swiveling ball joint 70, form the pendulous seal of the present invention.

As in previous embodiments, it is important that the pendulous module 40 be sealed to the housing 12 so that the only communication between the lumen of the cannula 14 and regions exterior of the trocar 10, is through the valves 56 and 58. Accordingly, in this embodiment, a circumferential or radial, preferably corrugated skirt 85 can be provided between the module 40 and the housing 12. This skirt 85 can be formed of a very thin, flexible material attached to the proximal portion of the elongate first seal member 81 or second seal member 83. The outer circumference of this skirt 85 can then be attached to the wall of the housing 12 to form a gas-tight seal between the housing and the pendent module 40. In further embodiments, the highly flexible coupler 65 may comprise a thin circular wiper seal or an O-ring seal between the socket 72 and the ball-joint 70.

Figure 14:
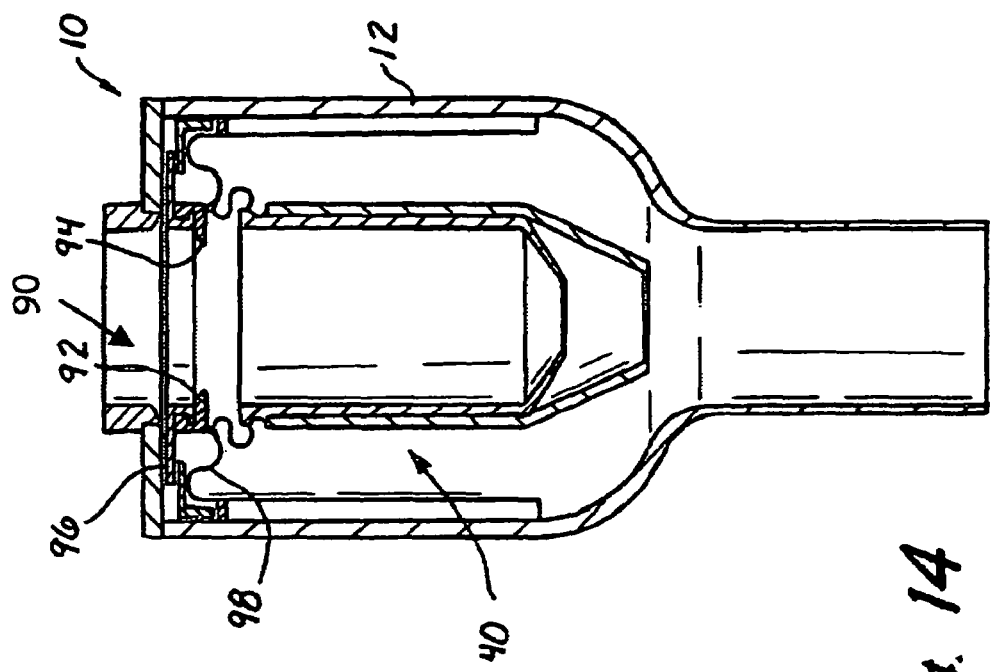
FIG. 14 is an axial cross-section view showing the pendent valve of FIG. 13 mounted in a seal housing of the trocar.
Figure 13:
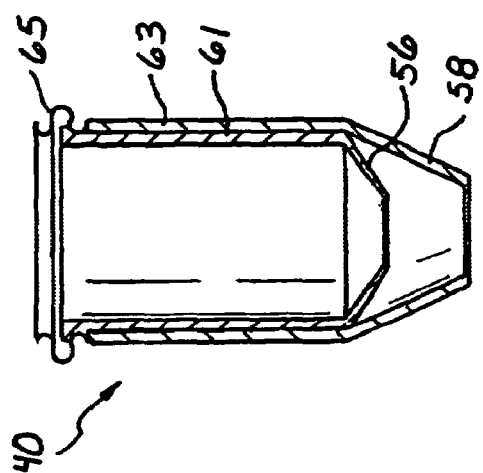
FIG. 13 is an axial cross-section view of a further embodiment of the pendent valve.
Figure 21:
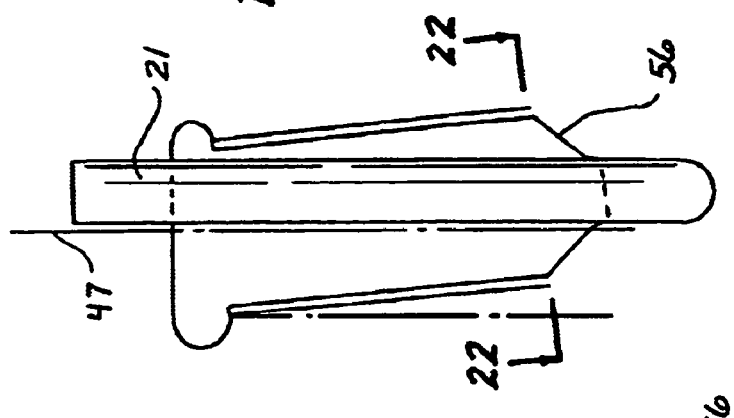
FIG. 21 is a schematic view of a pendent valve showing an instrument moved substantially off-axis without producing a cat-eye effect.

FIGS. 13 and 14 illustrate a further embodiment of the present invention where the pendulous seal module 40 is suspended upon a floating primary valve 90. In this case, the module 40 can be formed with the first tubular member 61, second tubular member 63, septum valve 56 and zero valve 58 and associated flexible coupler 65. The floating primary valve 90 will typically include a septum valve 92 with an orifice 94 which is configured to pass and seal around a large instrument with only minimal friction contact. The septum valve 92 is mounted on a structure 96 which is free to float in at least two dimensions. A flexible, typically corrugated skirt 98 forms a movable seal between the septum valve 92 and the housing 12 of the trocar 10. With these structural elements, the flexible coupler 65 of the module 40 can merely be attached to the septum valve 92 or skirt 98 to form a valve structure which is highly flexible and easily maneuverable. Note in particular that the floating primary valve 90 to which the module 40 is attached is itself capable of floating in at least two directions. Attaching the module 40, which itself floats in at least three directions, further accommodates the flotation desired to facilitate insertion and movement of an instrument without sacrificing the integrity of the various valve seals.

There is another aspect relating to operation of septum valves, such as the valve 56, that is illustrated in FIGS. 15 through 21. This aspect is the relationship of the septum orifice, such as the orifice 57, to an inserted instrument, such as the instrument 21. This relationship can be of particular importance since the valves of the trocar are commonly required to perform over a wide range of instrument sizes and shapes. The trocar valves must allow a laparoscopic surgeon to perform his or her tasks without undue interference or restriction attributable to the trocar valves. Therefore, in a preferred embodiment of the present invention, the septum orifice 57 is sized and configured to optimize the operation of the septum valve 56.

For example, the septum orifice 57 illustrated in FIGS. 15 and 16 is sized appropriately for a small or a large instrument 21. By way of example, the septum orifice 57 may have a diameter, perhaps even as large as 4.99 millimeters, in order to accommodate instrument diameters in a range between 5 and 12 millimeters. If the module 40 is restricted or fixed so that it does not pendulate, pivot, float, swivel, or otherwise move laterally, the orifice 57 will deform producing the undesirable cat-eye effect as a small instrument is maneuvered laterally as shown in FIGS. 17 and 18. The side-to-side pressure upon the orifice 57 will laterally stretch the septum 56, and the seal module 40 will fail.

Figure 22:
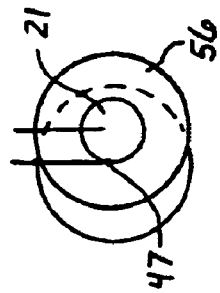
FIG. 22 is a cross-section view taken along lines 22—22 of FIG. 21.
Figure 20:
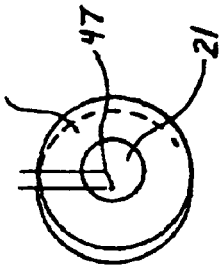
FIG. 20 is a cross-section view taken along lines 20—20 of FIG. 19.
Figure 19:
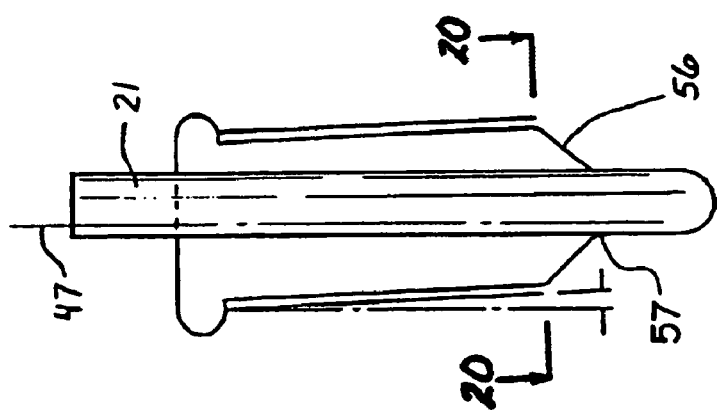
FIG. 19 is a schematic view of a pendent valve showing an instrument inserted slightly off axis without producing the cat-eye effect.
Figure 25:
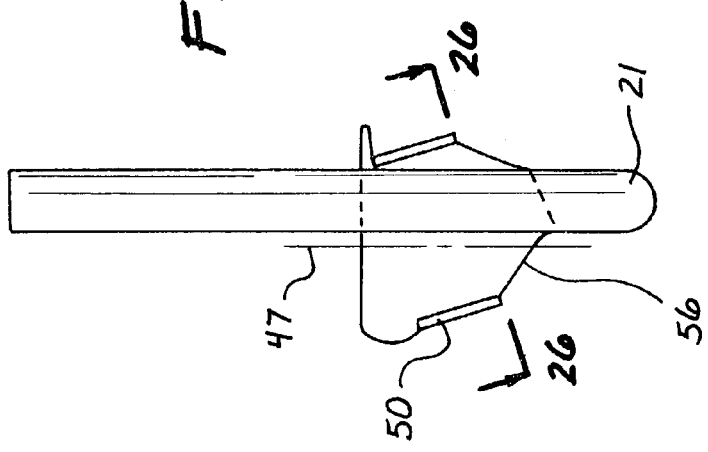
FIGS. 23–26 illustrate a comparison of side-load affects resulting from different lengths associated with a valve module.

Even if the seal module 40 is allowed to pivot, float or swivel, the force required to create that movement may be excessive in which case the orifice 57 will deform and the valve 56 will leak. It is therefore important in some preferred embodiments to provide the suspended or pendent module 40 with a construction that is laterally unrestricted at its distal end 54 so that the orifice 57 tends to follow the motion of the inserted instrument 21 without distortion or elongation. This favorable result is achieved in the embodiment of FIGS. 19 and 20 wherein the instrument 21 is removed slightly from the axis 47 without producing the cat-eye effect. This advantageous result is even more positively illustrated in FIGS. 21 and 22 wherein the instrument 21 is substantially removed from the axis 47 without producing the cat-eye effect.

Figure 26:
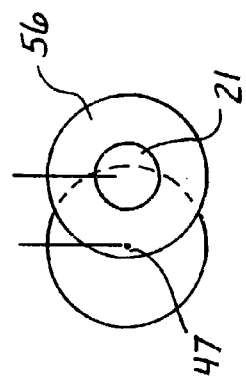
Figure 23:
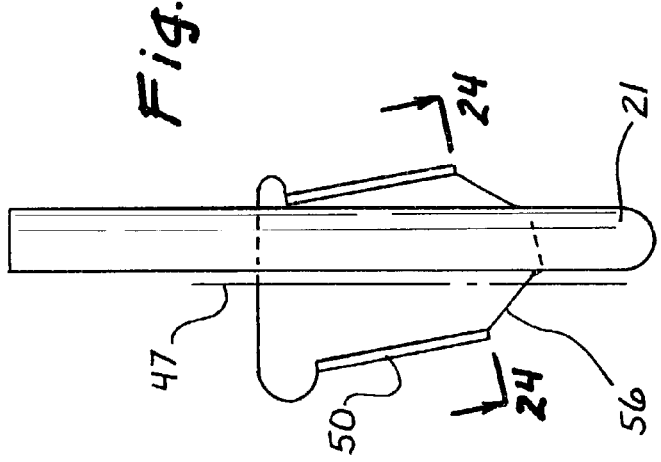
Figure 24:
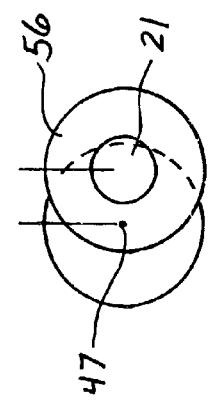

FIGS. 23 and 26 illustrate an embodiment where the highly flexible coupler 65 is provided at the proximal end 52 of the valve module 40. In these views, the length-to-diameter ratio of the module 40 is seen to be of importance. In order to facilitate this aspect, the length of the module 40 may exceed the diameter so that an appreciable leverage moment occurs in favor of lateral movement. The amount of side-to-side travel is illustrated in the respective FIGS. 24 and 26, where a long length of the module 40 is compared to a short length at the same diameter. In these figures, it can be seen that the longer length results generally in less side pressure on the orifice 57.

The length of the module 40, of course, is restricted by the size of the trocar 10. Nevertheless, the valve module 40 will typically have a length-to-diameter ratio greater than unity, and preferably at least two. Variations in this ratio may occur due to material choices or other construction elements that affect resistance to lateral movement.

Figure 27:
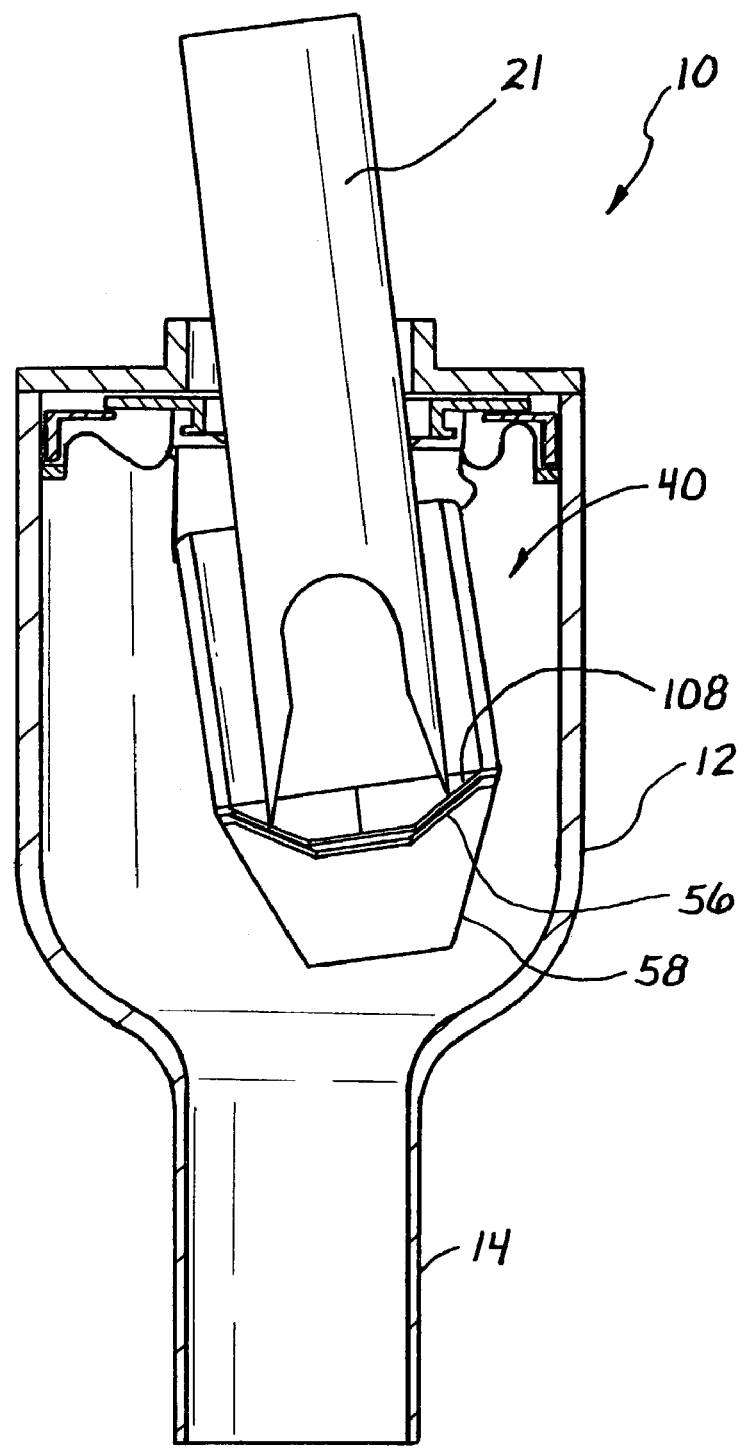
FIG. 27 illustrates a seal protection interface in a further embodiment.

Such construction elements might include a seal protector such as that designated by the reference numeral 108 in FIG. 27. This protector 108 is preferably mounted near or upon the proximal face of the septum valve 56. The protector 108 may include a plurality of semi-rigid overlapping leaves, levers, panels or the like that are sized and configured to provide an interface between the approaching instrument 21 and the septum valve 56. With this construction, the protector 108 can assume a large portion of the side-load of a small inserted instrument, such as the instrument 21, as it is maneuvered side-to-side in use.

Figure 29:
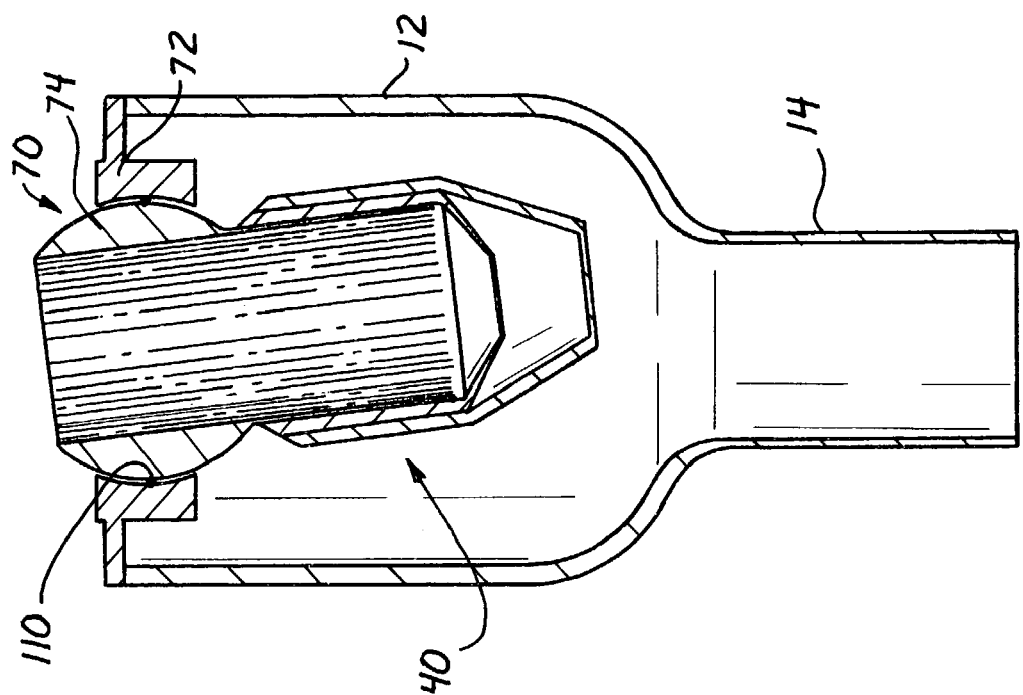
FIG. 29 illustrates an alternate embodiment having a swivel connection, with a side-load.
Figure 28:
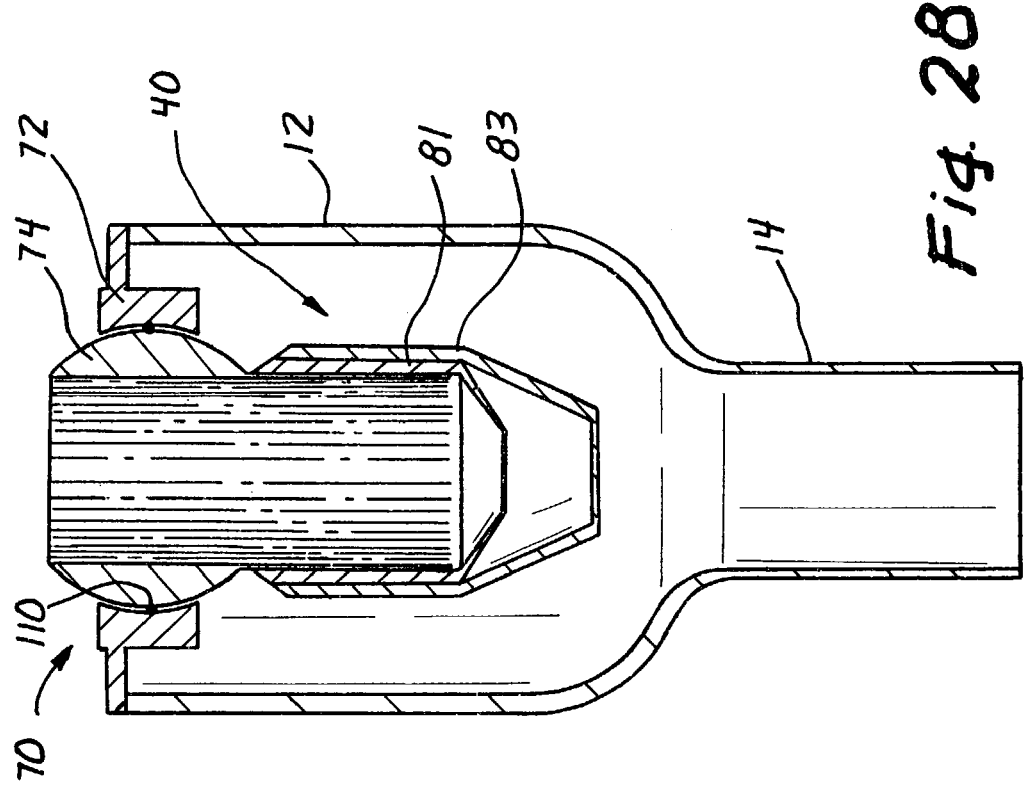
FIG. 28 illustrates an alternate embodiment having a swivel connection, at rest.

A further embodiment of the invention is illustrated in FIGS. 28 and 29. This embodiment is similar to that illustrated in FIGS. 11 and 12 and includes the housing 12, cannula 14, socket 72, and ball 74, as well as the first and second seal members 81 and 83, respectively. However, the skirt 85 is absent from the embodiment of FIG. 28, which relies upon other structure to form a seal between the seal module 40 and the housing 12. More specifically, in the illustrated embodiment, the ball joint 70 is produced with close tolerances, and the space between the socket 72 and the ball 74 is filled with a suitable lubricant 110. In this case, the lubricant not only forms the housing seal between the module 40 and the housing 12, but it also facilitates the desired floating movement of the ball 74 within the socket 72.

Figure 30:
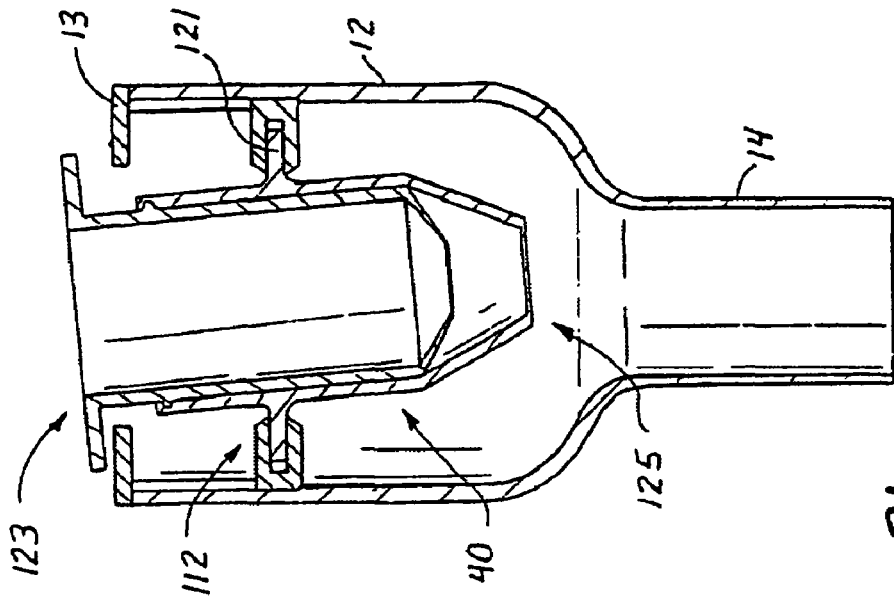
FIG. 30 is an axial cross-section view of a further embodiment wherein a valve module is pivotally supported between its distal end and its proximal end, the module being illustrated in an at-rest position.
Figure 31:
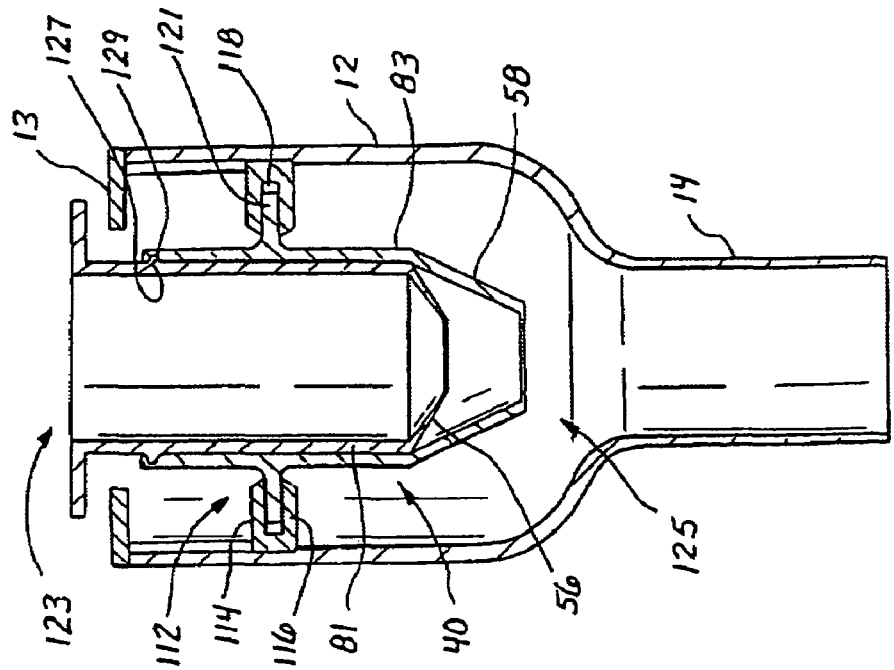
FIG. 31 is an axial cross-section view similar to FIG. 30 and illustrating the valve module pivoted in response to a side load.

Another embodiment is illustrated in FIGS. 30 and 31. This embodiment includes the housing 12 with the end cap 13 and cannula 14, as well as the seal module 40 with the first seal member 81 carrying the septum valve 56 and the second seal member 83 carrying the zero valve 58. In this embodiment, a support 112 is provided which couples the module 40 to the housing 12. In this case the support 112 includes flanges 114 and 116 which are fixed to the housing 12 and extend radially inwardly in a generally parallel relationship to define an annular recess 118. An annular flange 121, formed as part of the module 40, floats within the recess 118.

The location of the support 112 is of particular interest in this embodiment as it can be disposed generally anywhere between a proximal end 123 and a distal end 125 of the module 40. In the illustrated embodiment, the support 112 is disposed generally intermediate between these two ends 123 and 125. In general, the support 112 provides the only contact between the module 40 and the housing 12. As a result, both the proximal end 123 and the distal end 125 are free to float in three dimensions as they pivot about the support 112. The support 112 provides for flotation of the module 40 generally in two dimensions. As the ends 123 and 125 of the module 40 pivot relative to the sliding support 112 and the housing 12, a high degree of flotation can be achieved as illustrated in FIG. 31.

This embodiment also illustrates a construction of the module 40 wherein the first seal member 81 and the second seal member 83 are formed separately. In the subassembly illustrated, the first seal member 81 can be formed with an annular bead 127 and the second seal member 83 can be formed with an annular recess 129. With this construction, the second seal member 83 together with the angular flange 121 can be mounted on the first seal member 81, with the recess 129 registering with the bead 127.

An additional embodiment is illustrated in FIGS. 32–36. This embodiment is similar to those previously discussed in that it includes the housing 12, the cannula 14, as well as the module 40 and septum valve 25. In this case however, the zero valve 23 is not formed as part of the module 40 but rather is disposed across the working channel 18 in a fixed relationship to the housing 12. This embodiment offers the same advantage discussed with reference to FIG. 10 in that the end cap 13 can be removed with the module 40 thereby permitting the removal of large masses of tissue or other material from the surgical site. In the case of the FIG. 10 embodiment, the working channel 18 would be completely cleared resulting in the loss of insufflation.

Figure 34:
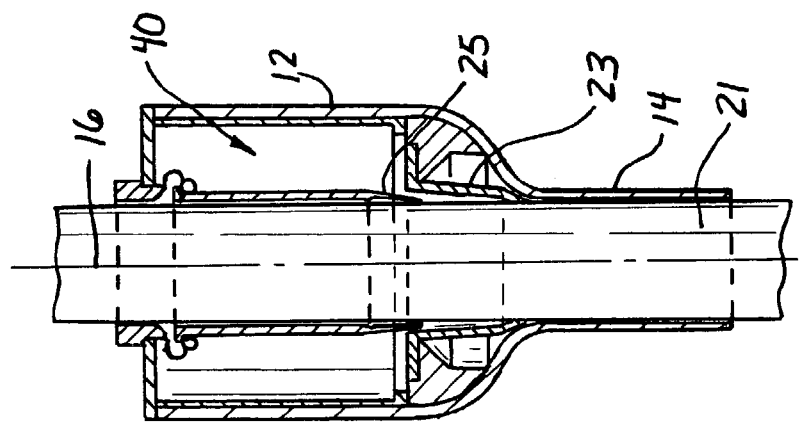
FIG. 34 is an axial cross-section view of the embodiment of FIG. 32 with an inserted instrument of relatively large diameter.
Figure 33:
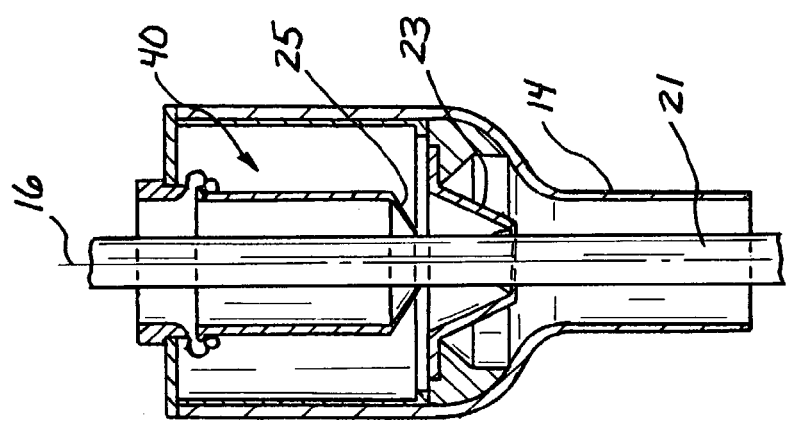
FIG. 33 is an axial cross-section view illustrating the valves of FIG. 32 with an inserted instrument of relatively small diameter.
Figure 32:
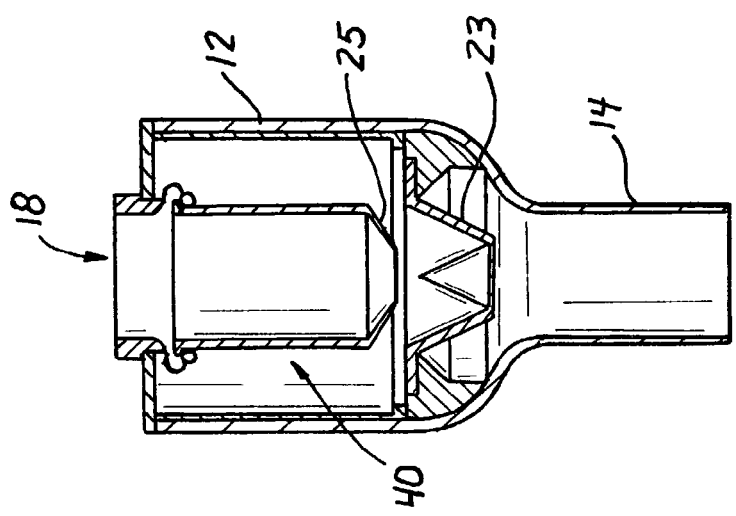
FIG. 32 is an axial cross-section view of a further embodiment including a pendent septum valve and a fixed zero valve.

If it is desired that insufflation be maintained, the embodiment of FIG. 32 will leave the zero valve 23 in place for that purpose. By way of design, the zero valve 23 will easily invert as tissue is removed; it will then automatically re-invert in order to maintain the desired insulation pressure. Also because the zero valve 23 is less delicate, its flotation is not as critical as that of the septum valve 25. Fixing the zero valve 23 within the housing 12 does not seem to degrade its function. In FIGS. 33 and 34, the trocar of FIG. 32 is illustrated with an inserted small instrument 21, and an inserted large instrument 21, respectively. In both cases, the instrument 21 is inserted along the axis 16 of the trocar.

Figure 35:
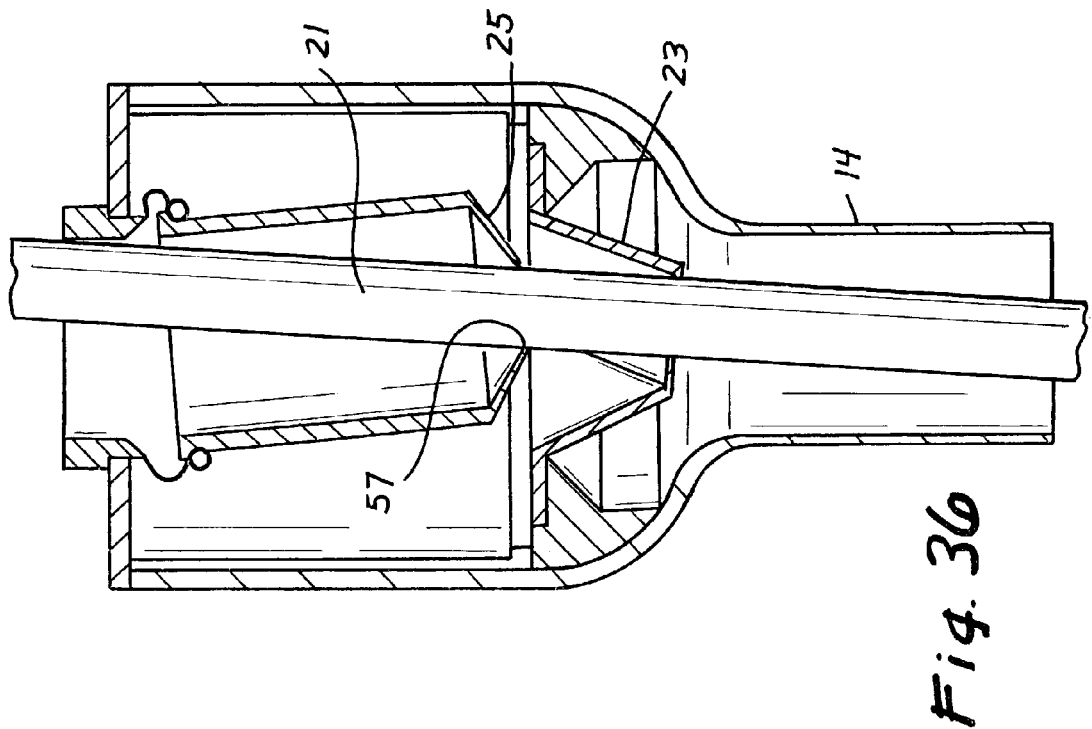
FIG. 35 is an axial cross-section view illustrating insertion of an instrument in the embodiment of FIG. 32.

A more realistic insertion of the instrument 21 is illustrated in FIG. 35 where the instrument 21 is inserted off-axis, at a severe angle to the trocar axis 16. Here again one can see the advantages provided by the pendulating module 40 which follows the instrument 21 to move the septum seal 25 into general alignment with the instrument 21 prior to penetration of the valve 25. As noted, the face angle is increased by the pendulating module 40 to further facilitate alignment with the orifice of the septum valve 25. Note that in this embodiment, the pendulating module 40 provides a high degree of flotation for the delicate septum valve 23 and 25. The zero valve 23 remains fixed within the housing 12.

Figure 36:
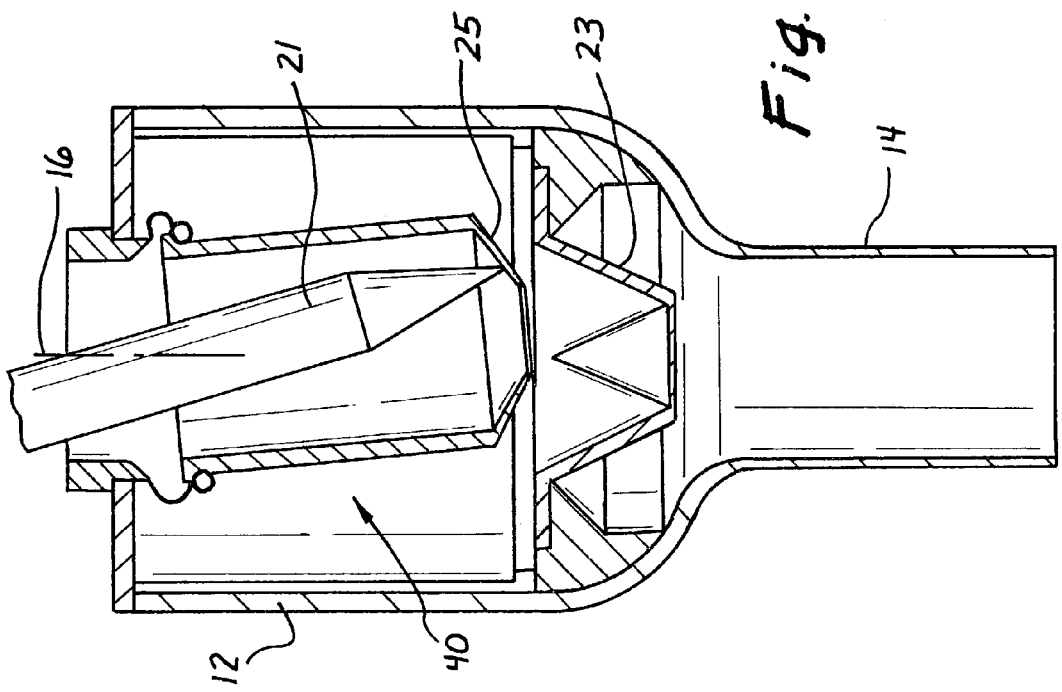
FIG. 36 is an axial cross-section view illustrating off-axis movement of an inserted instrument in the embodiment of FIG. 32.

After the instrument 21 is inserted, as illustrated in FIG. 36, it moves through the zero valve 23 and into the cannula 14. With the instrument totally inserted, the zero valve 25 no longer functions to maintain the insulation pressure. This function is transferred to the septum valve 23 which has formed an instrument seal with the instrument 21. As long as the instrument is in place, insufflation is maintained by the septum valve 23. In the manner previously discussed, maintenance of this instrument seal by the septum valve 23 is facilitated by the pendent module 40 which insures that the septum valve 23 is properly positioned to receive the instrument 21 through its orifice 57. Note that even in this embodiment, the zero valve 25 also functions to facilitate guidance as it works to move the instrument toward axial alignment. In the embodiment of FIG. 36, this guidance is performed distally of the septum valve 23 and independently of the module 40. In the embodiment of FIG. 5, the guidance function is performed distally of the septum valve 23 but in combination with the module 40.

In a further embodiment illustrated in FIGS. 37–44, the guidance function is performed proximally of the septum valve 56. In this case, the guidance function is performed by a leaf structure 130 that is disposed within the tube 50 proximally of the septum valve 56. This leaf structure 130 is perhaps best described with reference to FIG. 38 where the structure 130 is illustrated to include four leaves, the three illustrated having edges which normally extend radially inwardly to individual surfaces 132, 134 and 136, for example. As the instrument 21, is inserted through the guidance structure 130, these surfaces 132, 134, and 136 engage the instrument 21 following its angle of insertion and moving the tube 50 into a generally coaxially alignment with the instrument 21. As the tube 50 moves, the septum valve 56 is also moved so that its orifice 57 is aligned to receive the instrument 21. Note that in this embodiment the guidance structure 30 functions less to guide the instrument 21, and more to follow the instrument 21 and to guide the septum valve 56 into alignment.

Once the instrument 21 is inserted, the guidance structure 130 and tube 50 tend to maintain the instrument 21 and the septum valve 56 in coaxial alignment. This off-axis movement is illustrated in FIGS. 41–42. With the guidance structure 130 having the leaf configuration, instrument diameters can be easily accommodated as the leaves tend to fold outwardly. This is best illustrated in FIGS. 43–44. This structure provides a minimal area of contact with the instrument 21 regardless of diameter in order to inhibit friction forces on the instrument 21.

Of course the guidance function performed by the structure 130 can be accomplished by many other embodiments. Several examples are illustrated in FIGS. 45–50.

Figure 45:
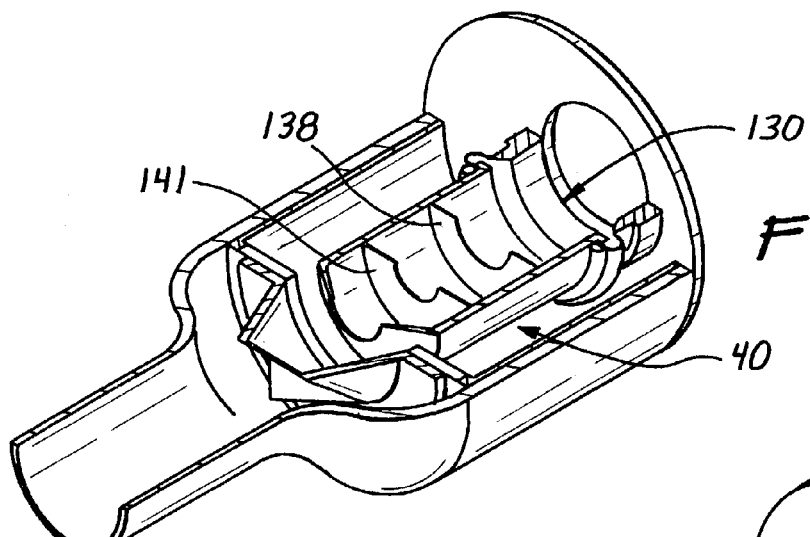
FIG. 45 is a perspective axial cross-section view wherein the proximal guidance structure including graduated annulus.

In FIG. 45, the guidance structure 130 includes a plurality of annuli 138 and 141 which are axially spaced within the tube 50 and have openings which decrease in diameter distally through the working channel. These annuli 138 and 141 function to provide increased guidance for the tube 50 and septum 56 as the instrument is moved through the module 40.

Figure 46:
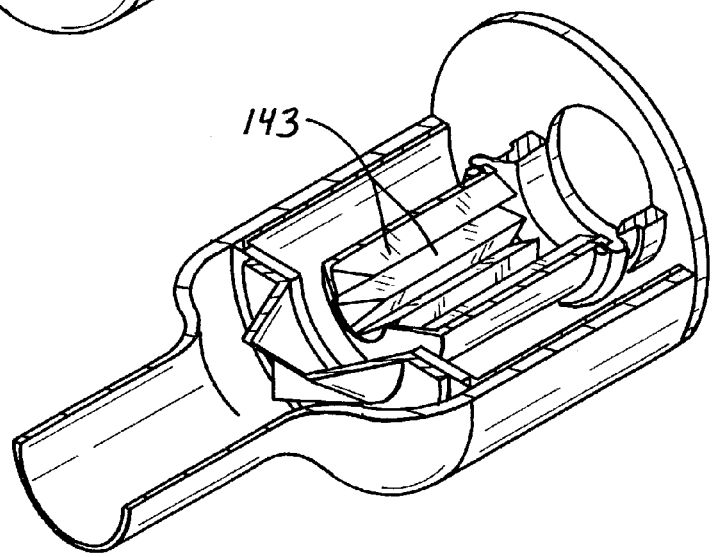
FIG. 46 is a perspective axial cross-section view wherein the proximal guidance structure includes a plurality of folds.

In the embodiment of FIG. 46, the guidance structure includes multiple axial corrugations 143, each of which extends inwardly to provide a line contact with the instrument 21 (not shown). This line contact further decreases any frictional forces which might be encountered upon insertion.

Figure 47:
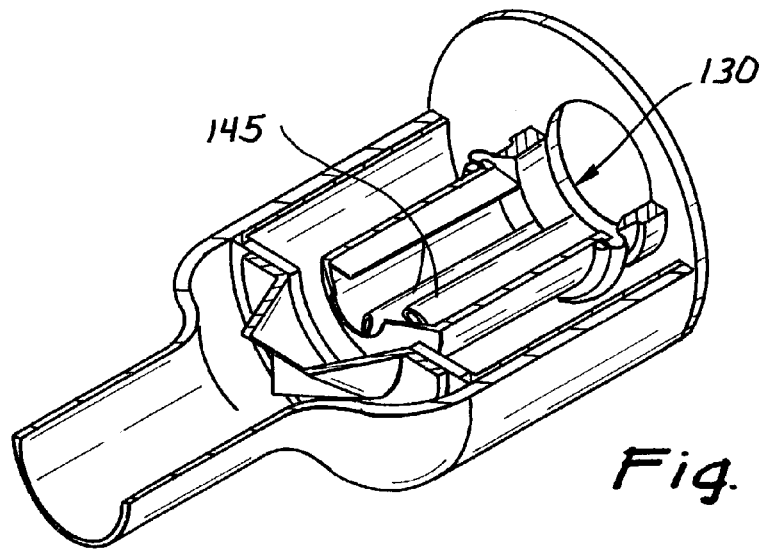
FIG. 47 is a perspective axial cross-section view wherein the proximal guidance structure includes a plurality of folded leaves.
Figure 48:
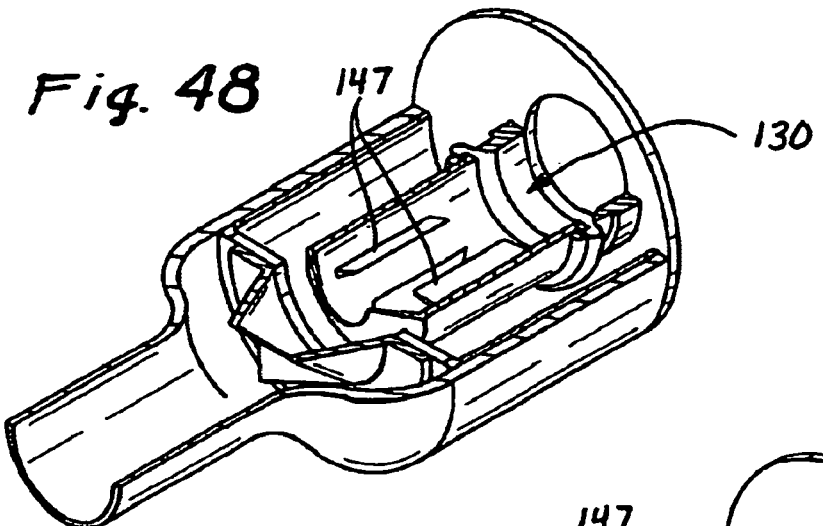
FIG. 48 is a perspective axial cross-section view wherein the proximal guidance structure includes a plurality of fins.
Figure 49:
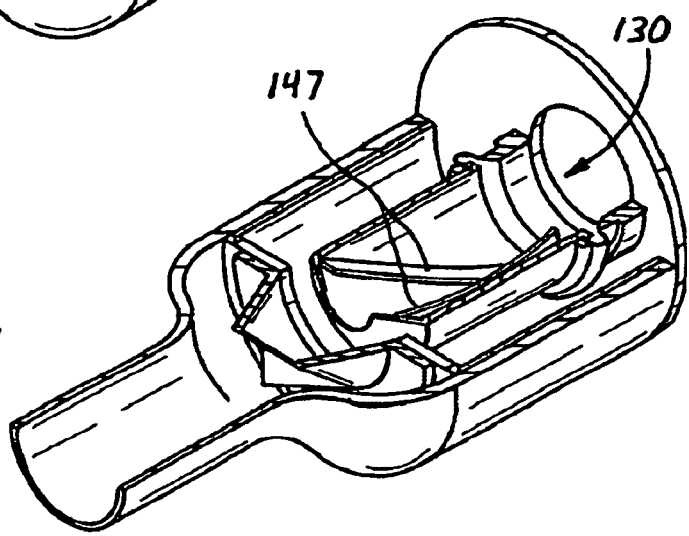
FIG. 49 is a perspective axial cross-section view wherein the proximal guidance structure includes at least one fin with a helical configuration.

In an embodiment similar to that illustrated in FIG. 47, a plurality of leaves are formed by individual axial elements 145 which extend radially inwardly and then are bent back on themselves to extend radially outwardly. A plurality of fins 147 form similar axial elements in the embodiment of FIG. 48. The fins 147 are positioned within the tube 50 to provide the guidance structure 130 with a spiral or helical configuration in the embodiment of FIG. 49.

Figure 50:
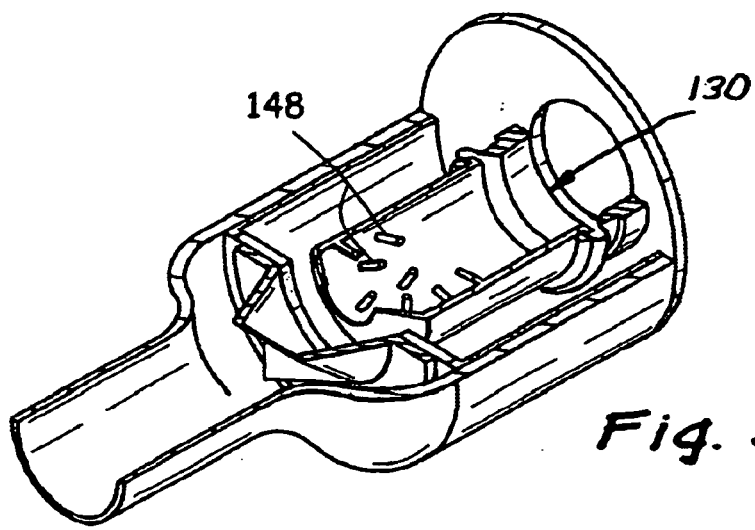
FIG. 50 is a perspective axial cross-section view wherein the proximal guidance structure includes a plurality of fingers.

In FIG. 50, a plurality of fingers 148 are provided to extend radially inwardly to contact an inserted instrument.

In each of these embodiments, the guidance structure 130 will typically be flexible so that it can accommodate a wide range of instrument diameters. Nevertheless, it needs to transfer a force from the instrument to move the tube 50 prior to penetration of the septum valve 56. Once the septum valve 56 is penetrated and the instrument is fully inserted, the guidance structure 130 will facilitate coaxial movement of the septum valve 56, not by pressure on the lip of the valve, but by pressure of the tube 50 on the perimeter of the valve 56.

With this discussion of only a few of the embodiments of the invention, it will be apparent that not all the features discussed will be required in a particular embodiment. In addition, the structures disclosed can be expected to offer other features and advantages not specifically mentioned. Furthermore, many of the same features will result from different structures and embodiments which have not been specifically discussed. As a result, one is cautioned not to restrict the scope of the present concept to only the embodiments and features discussed, but rather to determine the extent of the invention only with reference to the following claims.

The invention claimed is:

1. A surgical access device having a working channel adapted to receive a surgical instrument, comprising:
   a valve housing defining a working channel and including a side wall and an end wall;
   a valve module, flexibly coupled solely to a portion of the end wall, the portion of the end wall being perpendicular to the side wall;
   a connector flexibly coupling the valve module solely to the portion of the end wall; and
   the end wall of the housing being removable from the sidewall of the housing along with the valve module in order to leave the working channel generally unobstructed;
   wherein the valve module includes a septum valve;
   wherein the valve module further comprises a guilding structure responsive to movement of the instrument to adjust the valve toward a preferred orientation with the instrument;
   wherein the guiding structure includes an elongate tube having a diameter and a length not less than the diameter of the tube.

2. A surgical access device recited
   a valve housing defining a working channel and including a side wall and an end wall;
   a valve module, flexibly coupled solely to a portion of the end wall, the portion of the end wall being perpendicular to the side wall;

a connector flexibly coupling the valve module solely to the portion of the end wall; and the end wall of the housing being removable from the sidewall of the housing along with the valve module in order to leave the working channel generally unobstructed;

wherein the valve module includes a septum valve;

wherein the valve module further comprises a guiding structure responsive to movement of the instrument to adjust the valve toward a preferred orientation with the instrument;

wherein the guiding structure comprises a zero valve.

3. A surgical access device having a working channel adapted to receive a surgical instrument, comprising:

a valve housing defining working channel and including a side wall and an end wall;

a valve module, flexibly coupled solely to a portion of the end wall, the portion of the end wall being perpendicular to the side wall;

a connector flexibly coupling the valve module solely to the portion of the end wall; and the end wall of the housing being removable from the sidewall of the housing along with the valve module in order to leave the working channel generally unobstructed;

wherein the connector comprises a bellows.

4. A surgical device a valve housing defining a working channel and including a side wall and an end wall;

a valve module, flexibly coupled solely to a portion of the end wall the portion of the end wall being perpendicular to the side wall;

a connector flexible coupling the valve module solely to the portion of the end wall; and the end wail of the housing being removable from the sidewall of the housing along with the valve module in order to leave the working channel generally unobstructed;

wherein the valve module further comprises a septum valve, a zero valve and a tube having a distal end and a proximal end, the proximal end of the tube being coupled to the connector which is solely coupled to the portion of the end wall of the valve housing and the distal end of the tube being coupled to the septum valve and the zero valve.

5. A surgical access device having a working channel adapted to receive a surgical instrument, comprising:

a valve housing defining a working channel and including a side wall and an end wall;

a valve module, flexibly coupled solely to a portion of the end wall, the portion of the end wall being perpendicular to the side wall; and the end wall of the housing being removable from the sidewall of the housing along with the valve module in order to leave the working channel generally unobstructed;

wherein the valve module includes a septum valve, a guiding structure responsive to movement of the instrument to adjust the valve toward a preferred orientation with the instrument, the guiding structure including an elongate tube having a diameter and a length not less than the diameter of the tube and the elongate tube further comprises a first tubular member and a second tubular member coaxial with each other.

6. The surgical device recited in claim 5 further comprising a zero valve coupled to a distal end of the second tubular member and the first tubular member is coupled to a proximal end of the second tubular member.

7. A surgical device having an axis extending between a proximal end and a distal end, and having a working channel adapted to receive a surgical instrument, comprising:

a valve housing disposed along the working channel including a side wall and an end wall;

a valve assembly disposed in the valve housing and adapted to form an instrument seal with the surgical instrument when the surgical instrument is disposed in the working channel;

the valve assembly comprising:

a tube having an elongate configuration with a radial dimension and an axial dimension greater than the radial dimension, the tube defining at least a portion of the working channel in the valve assembly;

a connector coupling the end wall of the valve housing to the tube, and facilitating pendulous movement of the tube;

a septum valve carried by the tube and having properties for forming the instrument seal; and the septum valve being disposed a first distance from the connector, the first distance providing a first lever arm to facilitate movement of the tube and the septum valve in response to the movement of the surgical instrument within the working channel;

wherein the tube has a diameter and an axial length greater than the diameter.

8. The surgical device recited in claim 7 further comprising a guiding structure included in the valve assembly and being disposed at a second distance from the flexible connector to provide a second lever arm facilitating movement of the tube and the septum valve in response to movement of the surgical instrument.

9. The surgical device recited in claim 8, wherein the guiding structure is adapted to contact the instrument along at least one line to inhibit frictional forces between the valve assembly and the instrument.

10. The surgical device recited in claim 8 wherein the guiding structure comprises a zero valve having properties for sealing the working channel in the absence of the surgical instrument in the working channel.

11. The surgical device recited in claim 8, wherein the guiding structure has a rigidity greater than that of the septum valve.

12. The surgical device recited in claim 7, wherein the tube comprises a cylinder having a diameter and the first lever arm has a length greater than the diameter of the tube.

13. The surgical device recited in claim 7, wherein:

the tube has a distal end and a proximal end; and the connector forms the housing seal generally between the proximal end of the tube and the valve housing.

14. The surgical device recited in claim 13, wherein the septum valve is disposed generally at the distal end of the tube.

15. The surgical device recited in claim 7, wherein the connector has properties for floating the proximal end of the tube relative to the valve housing.

16. The surgical device recited in claim 7, wherein the distal end of the tube is generally pivotal about the connector and generally free to swing relative to the valve housing.

17. The surgical device recited in claim 7 wherein the connector comprises a bellows.

18. The surgical device recited in claim 7 wherein the end wall of the housing is removable from the sidewall of the housing along with the valve assembly in order to leave the working channel generally unobstructed.

* * * * *